(12) United States Patent
Redkar et al.

(10) Patent No.: US 6,492,379 B1
(45) Date of Patent: Dec. 10, 2002

(54) COMPOSITIONS AND FORMULATIONS OF 9-NITROCAMPTOTHECIN POLYMORPHS AND METHODS OF USE THEREFOR

(75) Inventors: Sanjeev Redkar, Union City, CA (US); Ashok Gore, San Ramon, CA (US)

(73) Assignee: Super Gen, Inc., Dublin, CA (US)

( * ) Notice: Subject to any disclaimer, the term of this patent is extended or adjusted under 35 U.S.C. 154(b) by 0 days.

(21) Appl. No.: 10/081,998

(22) Filed: Feb. 21, 2002

(51) Int. Cl.[7] .................. A61K 31/4738; C07D 491/147
(52) U.S. Cl. .......................................... 514/283; 546/48
(58) Field of Search ............................ 514/283; 546/48

(56) References Cited

U.S. PATENT DOCUMENTS 5,922,877 A * 7/1999 Cao ............................. 546/48

* cited by examiner

*Primary Examiner*—Charanjit S. Aulakh
(74) *Attorney, Agent, or Firm*—Wilson Sonsini Goodrich & Rosati

(57) ABSTRACT

A polymorphic form of 9-nitrocamptothecin is provided, the polymorph being characterizable as having, by differential scanning calorimetry, an endotherm at between 175.5 and 177.5° C., an exotherm at between 181.7 and 183.7° C., and an IR spectrum with no absorption centered between 3625 $cm^{-1}$ and 3675 $cm^{-1}$.

23 Claims, 29 Drawing Sheets

COMPOSITIONS AND FORMULATIONS OF 9-NITROCAMPTOTHECIN POLYMORPHS AND METHODS OF USE THEREFOR

FIELD OF THE INVENTION

This invention relates generally to compositions and formulations of 9-nitro-20-camptothecin polymorphs and methods for their in vivo delivery.

DESCRIPTION OF RELATED ART

Camptothecin was isolated from the plant, *Camptotheca acuminata*, in the 1960's (Wall, M. et al. (1966) *J. Am. Chem. Soc.* 88: 3888–3890). Camptothecin has a pentacyclic ring system with only one asymmetric center, in ring E, with a 20(S)-configuration. The pentacyclic ring system includes a pyrrole quinoline moiety (rings A, B and C), a conjugated pyridone (ring D), and a six-membered lactone (ring E) with an α-hydoxyl group.

Camptothecin itself is highly lipophilic and poorly water soluble. Sodium camptothecin solubilized by sodium hydroxide in water was used in clinical trials in the early 1970's and found to have antineoplastic activity, but as administered intravenously, caused unpredictable side effects such as myelosuppression and hemorrhagic cystitis. Clinical trials with sodium camptothecin were ultimately discontinued because of these toxicities and the lack of consistent antitumor activity.

Continued evaluation of camptothecin showed that the sodium carboxylate salt was only 10% as potent as the native camptothecin with the closed α-hydroxy lactone ring intact (Wall et al. "International Symposium on Biochemistry and Physiology of the Alkaloids, Mothes et al. eds. (1969) Academic Verlag, Berlin, 77; Giovanella et al. (1991) *Cancer Res.* 51:3052). Studies have demonstrated that camptothecin and its derivatives undergo an alkaline hydrolysis of the E-ring α-hydroxy lactone, resulting in a carboxylate form of camptothecin, but at pH levels below 7.0, the α-hydroxy lactone E-ring form of camptothecin predominates. An intact lactone ring E and α-hydoxyl group have been shown to be essential for antitumor activity of camptothecin and its derivatives.

Camptothecin and its derivatives have been shown to inhibit DNA topoisomerase I by stabilizing the covalent complex ("cleavable complex") of enzyme and strand-cleaved DNA. Inhibition of topoisomerase I by camptothecin induces protein-associated DNA single-strand breaks, which occur during the S-phase of the cell cycle. Because the S-phase is short relative to other cell cycle phases, the toxicity per cell cycle is relatively low, and therefore more acceptable for slowly dividing cells. Exposure to camptothecin for a specified period of time would result in increased cytotoxicity of tumor cells, which divide at a more rapid rate.

Studies indicate that only the closed α-hydroxy lactone form of the drug helps stabilize the cleavable complex, leading to inhibition of the cell cycle and apoptosis. To preserve the α-hydroxy lactone form of camptothecin, camptothecin and its water insoluble derivatives have been dissolved in N-methyl-2-pyrrolidinone in the presence of an acid (U.S. Pat. No. 5,859,023 to Hausheer et al.). Upon dilution with an acceptable parenteral vehicle, a stable solution of camptothecin was obtained. The concentrated solution of camptothecin was also filled in gel capsules for oral administration. It is believed that such formulations increase the amount of lipophilic α-hydroxy lactone form of camptothecin that diffuse through the cellular and nuclear membranes in tumor cells.

Various substituted forms of 20 (S)-camptothecin have been evaluated for antineoplastic activity. Good activity was found for various substitutions to the 20(S)-camptothecin scaffold. For example, 9-Amino-20(S)-Camptothecin ("9AC") and 10,11-methylendioxy-20(S)-camptothecin ("10,11, MD") are capable of having high anticancer activity against human colon cancer xenografts. (Giovanella, B. C., et al., "Highly effective topoisomerase-I-targeted chemotherapy of human colon cancer in xenografts." (1989) *Science* 246:1046–1048).

Additionally, 9-nitro-20(S)-camptothecin (referred to herein as "9-nitrocamptothecin" and often abbreviated in the literature as "9-NC"), which has a nine position hydrogen substituted with a nitro moiety, has shown high activity against human tumor xenograft models. 9-nitrocamptothecin may be obtained, for example, by extracting the naturally occurring compound from the plant *C. acuminata*, according to the method of Wall et al. (1966), supra, and substituting a nitro moiety for hydrogen at the nine ring position by known synthetic organic methods (see for example U.S. Pat. No. 5,922,877 to Cao). 9-nitrocamptothecin has inhibited the growth of human tumor xenografts in immunodeficient nude mice and has also induced regression of human tumors established as xenografts in nude mice with little or no appearance of any measurable toxicity. (D. Chatterjee et al., "Induction of Apoptosis in Malignant and Camptothecin-resistant Human Cells," (1996) *Annals of the New York Academy of Sciences* 803: 143). Thus, a continuing need exists for new and improved ways to exploit the useful therapeutic activities of 9-nitrocamptothecin and its various derivatives and analogs.

SUMMARY OF THE INVENTION

The present invention provides novel polymorphs of 9-nitrocamptothecin, including both crystalline and amorphous forms, as well as pharmaceutical compositions and formulations comprising these polymorphs. In one variation, the pharmaceutical compositions and formulations are adapted for administration via oral, injection and inhalation. Various methods are also provided including methods of making the disclosed 9-nitrocamptothecin polymorphs, methods for manufacturing pharmaceutical formulations and compositions comprising the polymorphs, as well as methods of using the pharmaceutical preparations to treat various diseases.

In one embodiment, a 9-nitrocamptothecin polymorph is provided that may be crystallized from acetone or dichloromethane. This polymorph may be characterized by one or more of the following physical properties. The polymorph exhibits an X-ray powder diffraction pattern with salient features being major diffraction lines at °2θ values 8.0 and 25.7 for Cu Kα radiation of wavelength 1.5406 Angstrom. Other notable features of the characterization data of this polymorph include: by differential scanning calorimetry, an endotherm at between about 175.5 and 177.5° C., an exotherm at between about 181.7 and 183.7° C., and an IR spectrum with no absorption centered between about 3625 $cm^{-1}$ and 3675 $cm^{-1}$.

In another embodiment, a 9-nitrocamptothecin polymorph is provided that may be crystallized from tetrahydrofuran. This polymorph may be characterized by one or more of the following physical properties. The polymorph exhibits an X-ray powder diffraction pattern with salient features being major diffraction lines at °2θ values 6.7, 12.5, 14.0 and 23.9 for Cu Kα radiation of wavelength 1.5406 Angstrom. Other notable features of the characterization data of this polymorph include: by differential scanning calorimetry, no observable endotherm and an exotherm at between about 273.6 and 275.6° C., and a solution NMR spectrum with multiplets at about 1.7 and 3.7 ppm shifts.

In another embodiment, a 9-nitrocamptothecin polymorph is provided that may be crystallized from acetonitrile. This polymorph may be characterized by one or more of the following physical properties. The polymorph exhibits, for Cu Kα radiation of wavelength of 1.5406 Angstrom, an X-ray powder diffraction pattern with salient features being major diffraction lines at °2θ values 4.8, 14.2, 19.1 and 26.8. Other notable features of the characterization data of this form include: by differential scanning calorimetry, an endotherm at between about 273.9 to 275.9° C., and an exotherm at between about 279.3 and 281.3° C.

In another embodiment, a 9-nitrocamptothecin polymorph is provided that may be formed by crystallizing 9-nitrocamptothecin from acetone, dichloromethane, tetrahydrofuran or acetonitrile to form an initial product, and then recrystallizing the initial product from a solvent comprising a mixture of dimethylformamide and water. This polymorph may be characterized by one or more of the following physical properties. The polymorph exhibits for Cu Kα radiation of wavelength of 1.5406 Angstrom, an X-ray powder diffraction pattern having salient features being major diffraction lines at °2θ values 11.0, 14.0, 16.4 and 27.0. Other notable features of the characterization data of this form include: an IR spectrum with an absorption centered between about 3625 $cm^{-1}$ and 3675 $cm^{-1}$ and content of more than a trace of water.

In another embodiment, a 9-nitrocamptothecin polymorph is provided that may be crystallized from substantially water free dimethyformamide. This polymorph may be characterized by one or more of the following physical properties. The polymorph exhibits an X-ray powder diffraction pattern having salient features being diffraction lines at °2θ values 5.4, 10.6 and 26.5 for Cu Kα radiation having a wavelength of 1.5406 Angstrom. Other notable features of the characterization data of this form include: by differential scanning calorimetry, an endotherm at between about 149.2 and 151.2° C., an exotherm at between about 162.6 and 164.6° C., and an exotherm at between 272 and 274° C.

Yet other 9-nitrocamptothecin polymorphs are provided that are wholly amorphous or are crystalline with increased amorphous content compared to the directly crystallized polymorph as a result of grinding or pulverization. A wholly amorphous polymorph may be obtained by rapid evaporation of solvent from a 9-nitrocamptothecin solution in methanol. This polymorph exhibits no discernable X-ray powder diffraction pattern, comprises a glass. Increased amorphous content polymorphs include the polymorph obtained by crystallization from ethanol followed by grinding, which exhibits, for Cu Kα radiation of wavelength 1.5406 Angstrom, an X-ray powder diffraction pattern with salient features being major diffraction lines at °2θ values 10.5 and 12.2, said lines being broadened to at least 1.2 times the breadth at half radiation signal amplitude of an X-ray powder diffraction pattern obtained by crystallizing 9-nitrocamptothecin from ethanol.

DETAILED DESCRIPTION OF THE INVENTION

Figure 1:
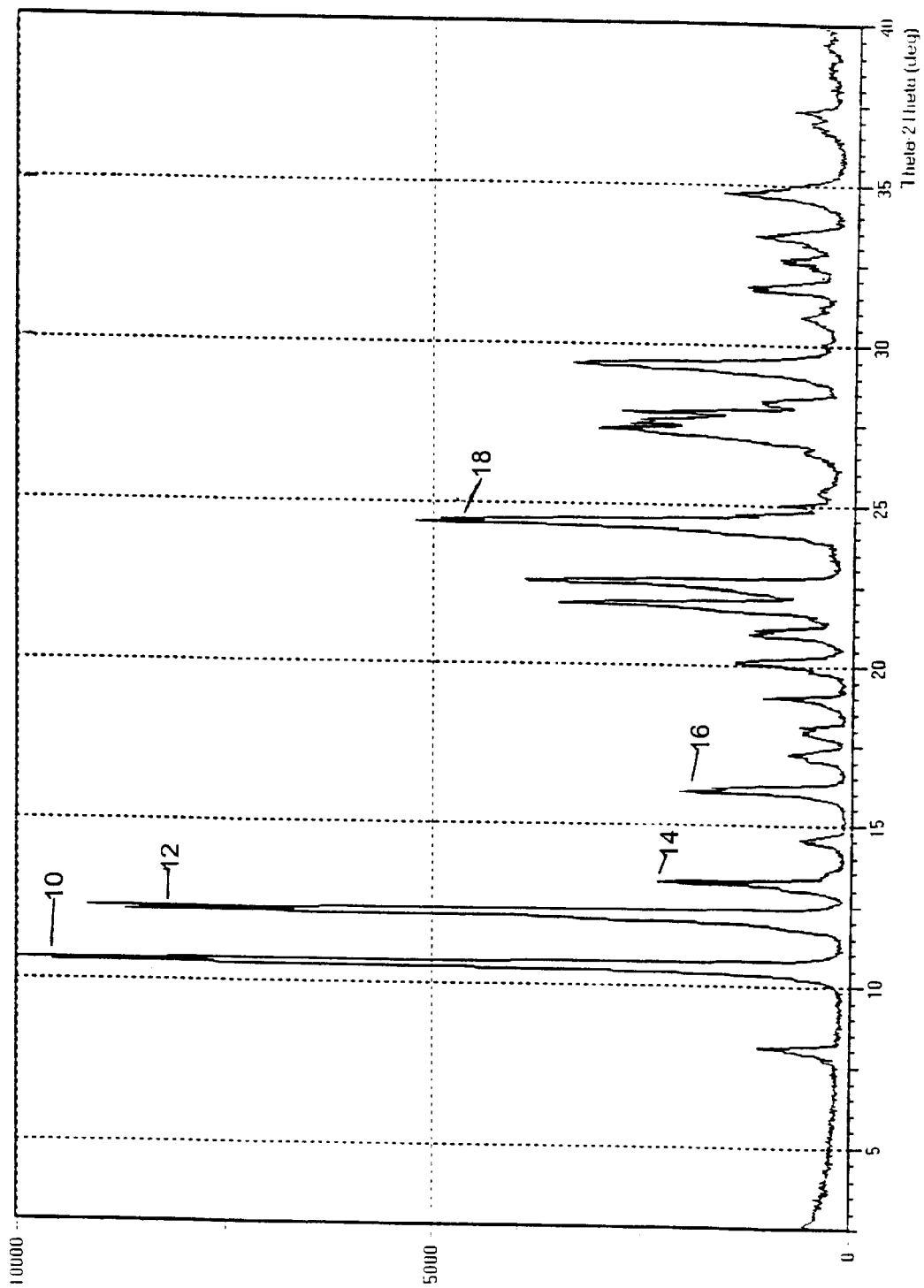
FIG. 1 illustrates the XRPD pattern of Form A (the "XRPD pattern" being a plot of the intensity of diffracted lines.

The present invention provides novel polymorphs of 9-nitrocamptothecin, including both crystalline and amorphous forms, as well as pharmaceutical compositions and formulations comprising these polymorphs. In one variation, the pharmaceutical compositions and formulations are adapted for administration via oral, injection and inhalation. Various methods are also provided including methods of making the disclosed 9-nitrocamptothecin polymorphs, methods for manufacturing pharmaceutical formulations and compositions comprising the polymorphs, as well as methods of using the pharmaceutical preparations to treat various diseases.

Definitions

As used herein, "amorphous" refers to a material that contains too little crystal content to yield a discernable pattern by XRPD or other diffraction techniques. Glassy materials are contemplated to be amorphous. Amorphous materials do not have a true crystal lattice, and are consequently glassy rather than true solids, technically resembling very viscous non-crystalline liquids. Rather than true solids, glasses may better be described as quasi-solid amorphous material. Thus an amorphous material refers to a quasi-solid glassy material. Precipitation of a compound from solution, often effected by rapid evaporation of solvent, is known to favor amorphous forms of a compound.

The term "broad" or "broadened" as used herein to describe spectral lines including XRPD, NMR and IR spectroscopy lines is a relative term that relates to the line width of a baseline spectrum. The baseline spectrum is often that of an unmanipulated crystalline (defined below) form of a specific compound as obtained directly from a given set of physical and chemical conditions, including solvent composition and properties such as temperature and pressure, for example describing the XRPD spectrum of ground or pulverized crystalline material relative to the crystalline material prior to grinding. In materials where the constituent molecules, ions or atoms, as solvated or hydrated, are not tumbling rapidly, line broadening is indicative of increased randomness in the orientation of the chemical moieties of the compound, thus indicative of an increased amorphous content. When comparisons are made between crystalline materials obtained via different crystallization conditions, broadening indicates either increased amorphous content of the sample having the broadened spectral lines, or possibly a mixture of crystals that have similar, although not identical spectra.

As used herein, "crystalline" refers to a material that contains a specific compound, which may be hydrated and/or solvated, and has sufficient crystal content to exhibit a discernable diffraction pattern by XRPD or other diffraction techniques. Often, a crystalline material that is obtained from a solvent by direct crystallization of a compound dissolved in a solution or interconversion of crystals obtained under different crystallization conditions, will have crystals that contain the solvent, termed a crystalline solvate. Also, the specific solvent composition and physical properties of crystallization, collectively termed crystallization conditions, may result in crystalline material having physical and chemical properties that are unique to the crystallization conditions. Examples of crystal properties include orientation of the chemical moieties of the compound with respect to each other within the crystal and predominance of a specific form of the compound, for example the lactone form of 9-nitrocamptothecin, which is favored by the presence of an acid in the solvent composition.

Depending upon the form of the specific type of crystal present, which dictates the thermodynamic stability of the crystal, various amounts of amorphous solid material containing the specific compound will be present, as a side product of the initial crystallization, and/or a product of degradation of the crystals comprising the crystalline material. Thus crystalline as used herein contemplates amorphous content of varying degrees so long as the material has a discernable diffraction pattern. Often the amorphous content of a crystalline material may be increased by grinding or pulverizing the material, which is evidenced by broadening of diffraction and other spectral lines relative to the unground crystalline material. Sufficient grinding and/or pulverizing may broaden the lines relative to the unground crystalline material to the extent that the XRPD or other crystal specific spectrum may become undiscernable, making the material substantially amorphous, or barely discernable, which may be termed quasi-amorphous.

As contemplated herein the term "trace" refers to an amount that is detectable by the physical and chemical detection methods employed herein, but comprises less than 0.03 of an equivalent of the specific compound present in the crystal. For example a crystalline polymorph of 9-nitrocamptothecin containing less than 0.04% (w/w) $H_2O$ where a crystal containing one $H_2O$ molecule per molecule of 9-nitrocamptothecin, e.g. one equivalent of $H_2O$ would be approximately 4.4% (w/w) $H_2O$ is correctly described as containing a trace of water.

1. Polymorphs of 9-Nitrocamptothecin

Described herein are various polymorphs according to the present invention. These polymorphs include crystalline (e.g. true solid) and amorphous (e.g. glassy or quasi-solid) polymorphic forms. For ease, several of the polymorphs described herein are designated A through G and consistently referenced thereby. In order physically characterize the polymorphs, various tests were performed including x-ray powder diffraction ("XRPD"), differential scanning calorimetry ("DSC"), thermogravimetry analysis ("TGA"), hot stage microscopy, infrared spectrometry ("IR"), Raman spectrometry and Karl Fischer analysis. Where possible, the results of each test for the different polymorph is provided.

A. General Methods of Precipitation, Crystallization, Interconversion Employed in Making 9-Nitrocamptothecin Polymorphs Polymorphs according to the present invention may be obtained by direct crystallization of 9-nitrocamptothecin or by crystallization followed by interconversion. In some instances, the polymorphs are crystalline and in others amorphous. Amorphous polymorphs may also be derived by rapidly evaporating solvent from solvated 9-nitrocamptothecin, or by grinding, pulverizing or otherwise physically pressurizing or abrading the various crystalline polymorphs described herein. General organic methods for precipitating and crystallizing organic compounds may be applied to preparing the various 9-nitrocamptothecin polymorphs. These general methods are known to those skilled in the art of synthetic organic chemistry and pharmaceutical formulation, and are described, for example, by J. March, "Advanced Organic Chemistry: Reactions, Mechanisms and Structure," 4th Ed. (New York: Wiley-Interscience, 1992).

B. Form A polymorph of 9-nitrocamptothecin

Form A polymorph of 9-nitrocamptothecin may be made by crystallizing 9-nitrocamptothecin from reagent or HPLC grade ethanol. For example, a saturated or near saturated solution of 9-nitrocamptothecin in ethanol may be prepared. The 9-nitrocamptothecin in the saturated or near saturated solution of ethanol may then be crystallized employing conventional methods for crystallizing organic compounds from organic solvents.

FIG. 1 illustrates the XRPD pattern of Form A. Major diffraction lines 10 and 12 are observed at approximately 10.5 and 12 °2θ respectively. Sharp, but weaker lines 14, 16 and 18 are observed at 13.25, 16, and 24.5 °2θ and several broader and weaker lines are observed as well.

Form A exhibits a needle morphology. Consistent with this, most of the XRPD data on Form A exhibit preferred orientation effects, observed as variations in relative peak intensity, which are often observed in crystalline materials having a needle or plate morphology.

Thermogravimetric and DSC data on form A is summarized below in Table 1 and plotted in FIG. 2.

TABLE 1

Thermal Data on Crystal Form A

| Form | DSC Results* | TGA Results** |
|---|---|---|
| A | Endo 278.3, exo 283.9 | <0.1 |

*endo - endotherm, exo - exotherm, maximum temperature reported for transition
**percent weight change from 35 to 200° C.

Figure 2:
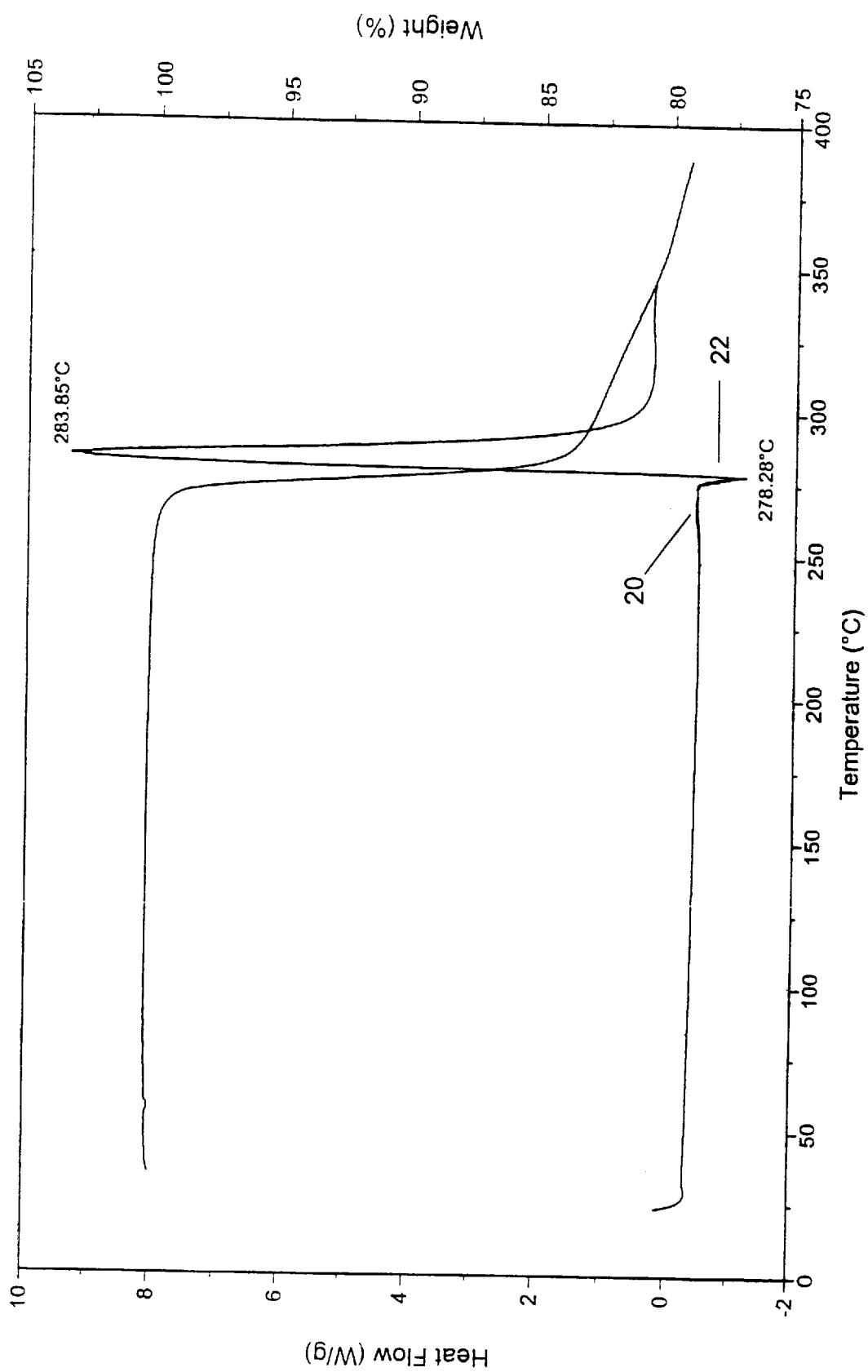
FIG. 2 is a plot of TGA data and the DSC data for Form A.

Making reference now to FIG. 2, no weight loss was observed prior to decomposition above 250° C. A minor exotherm 20 is observed in the DSC curve at a temperature just below the melt endotherm 22 at 278.3° C. and may be due to some decomposition or crystal reordering during or just prior to the melt. This melt is confirmed by hot stage data, summarized below in Table 2.

TABLE 2

Hot Stage Microscopy Observations

| Form | Sample # | Observations |
|---|---|---|
| A | 1 | Needles darken at 210° C., melt onset 264° C., melt at 267° C., solid does not recrystallize at RT. |
| A | 2 | Needles, melt onset 262° C., melt with bubble 266° C., solid does not recrystallize. |

Figure 3:
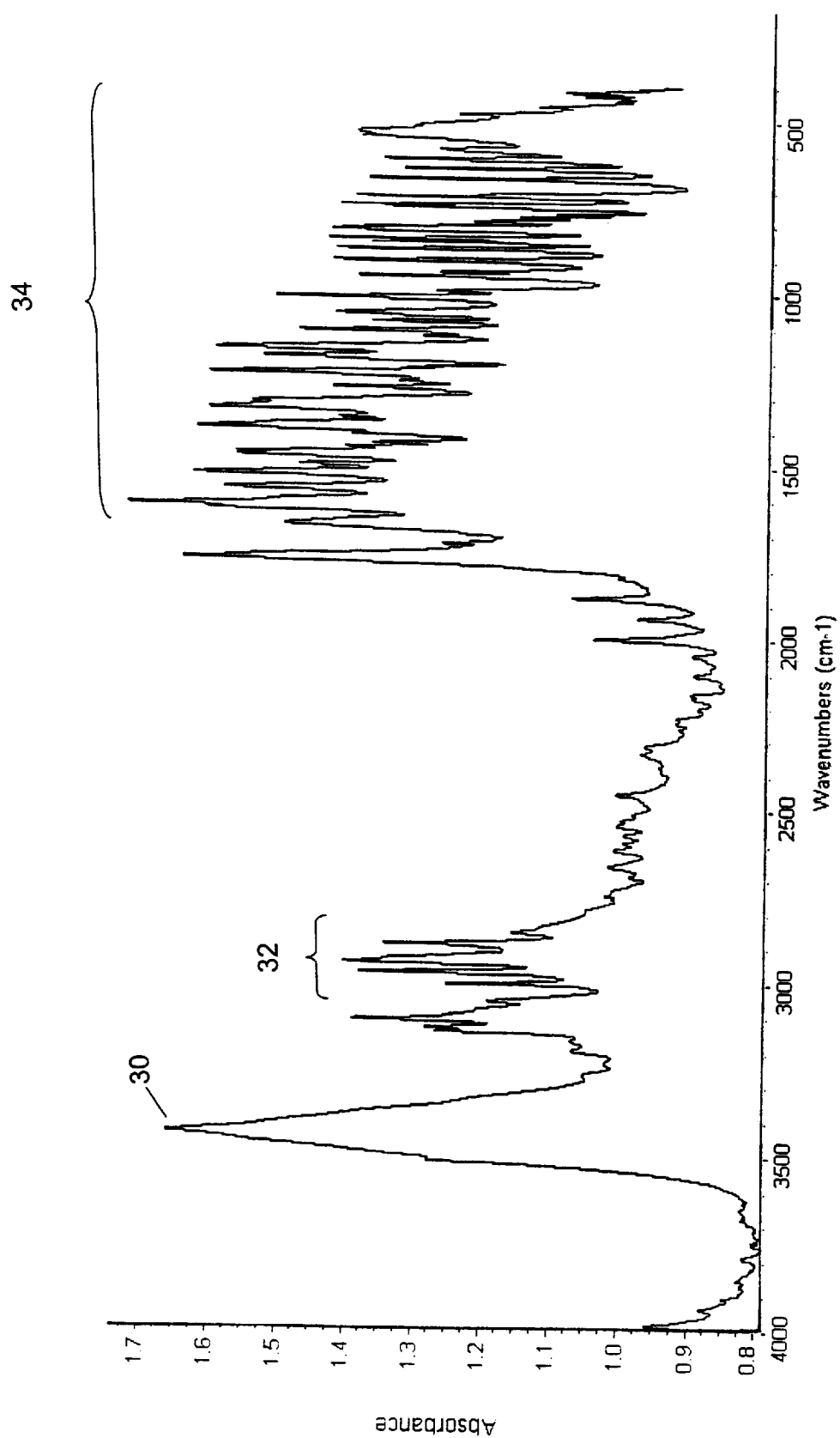
FIG. 3 is a plot of the IR absorption spectrum for Form A.

The IR spectrum for Form A is plotted in FIG. 3. The spectrum shows a relatively sharp OH stretch 30 around 3430 $cm^{-1}$, aromatic and aliphatic CH stretches 32 between 3100 and 2800 $cm^{-1}$, and a very complex fingerprint region 34 from 1700–400 $cm^{-1}$.

Figure 4:
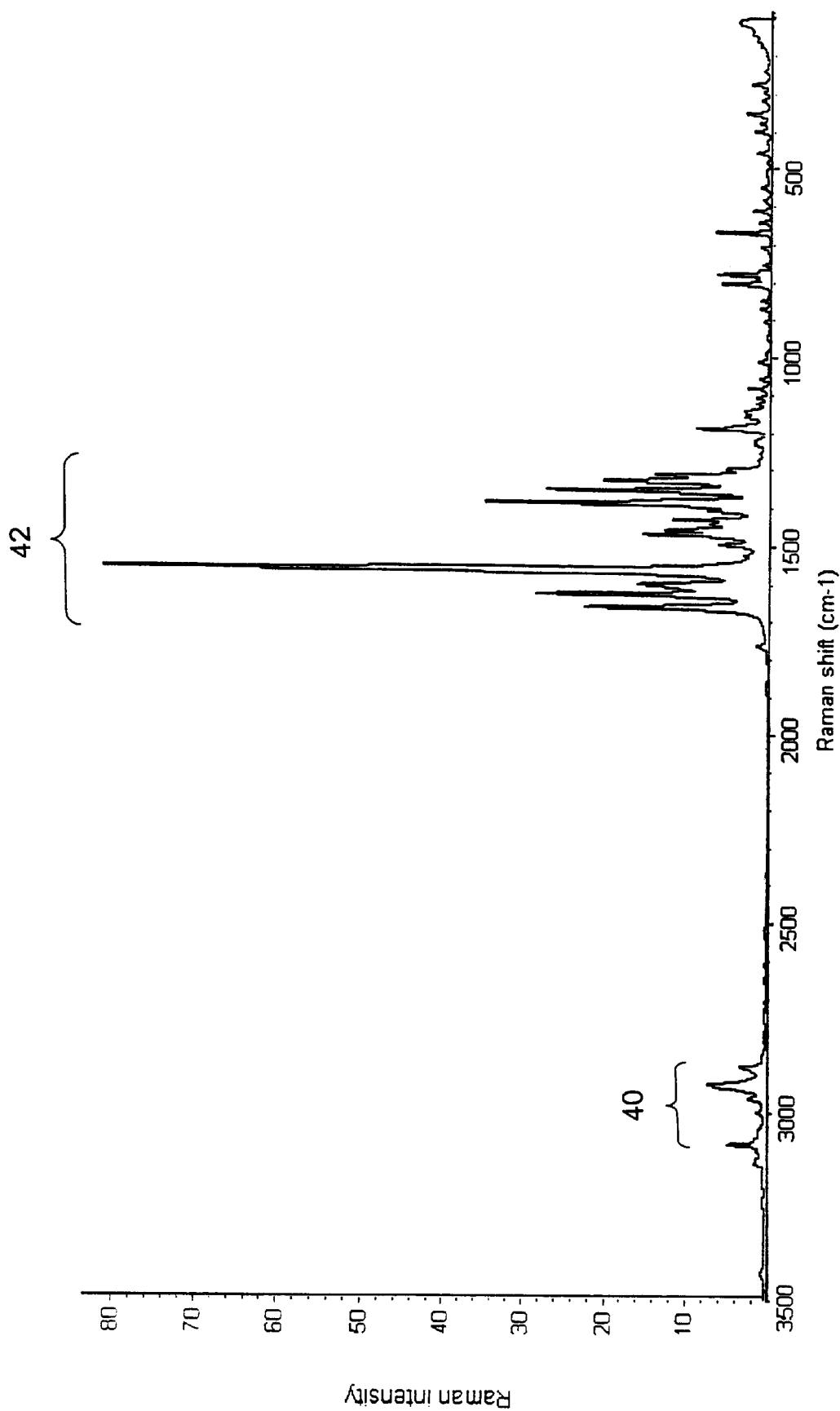
FIG. 4 is a plot of the Raman absorption spectrum for Form A

The Raman spectrum for Form A is provided in FIG. 4. The Raman spectrum shows relatively weak aromatic and aliphatic CH stretches 40 between 3100 and 2800 $cm^{-1}$, and stronger bands 42 in the region from 1700–1300 $cm^{-1}$.

Data of moisture sorption/desorption for Form A are summarized below in Table 3.

TABLE 3

Moisture Sorption/Desorption Data for Form A.

| Elap Time Min | Weight Mg | Weight % chg | Samp Temp Deg C. | Samp RH % |
|---|---|---|---|---|
| 0.0 | 12.3086 | 0.0000 | 24.99 | 14.41 |
| 11.1 | 12.3102 | 0.0131 | 25.02 | 5.16 |
| 19.6 | 12.3104 | 0.0149 | 25.02 | 15.27 |
| 27.2 | 12.3107 | 0.0169 | 25.03 | 24.98 |
| 34.7 | 12.3112 | 0.0210 | 25.03 | 35.07 |
| 42.2 | 12.3116 | 0.0242 | 25.03 | 45.07 |
| 50.2 | 12.3121 | 0.0283 | 25.03 | 55.00 |
| 59.2 | 12.3125 | 0.0315 | 25.03 | 64.96 |
| 68.3 | 12.3129 | 0.0347 | 25.03 | 74.75 |
| 77.3 | 12.3134 | 0.0387 | 25.03 | 84.64 |
| 86.3 | 12.3138 | 0.0421 | 25.03 | 94.90 |
| 94.8 | 12.3139 | 0.0429 | 25.03 | 84.95 |
| 103.8 | 12.3139 | 0.0429 | 25.03 | 75.18 |
| 111.8 | 12.3136 | 0.0405 | 25.02 | 65.02 |
| 119.8 | 12.3133 | 0.0381 | 25.02 | 54.99 |
| 127.8 | 12.3132 | 0.0372 | 25.02 | 45.05 |
| 135.8 | 12.3129 | 0.0348 | 25.02 | 34.97 |
| 143.3 | 12.3126 | 0.0324 | 25.02 | 24.95 |
| 150.3 | 12.3124 | 0.0307 | 25.03 | 15.00 |
| 157.3 | 12.3120 | 0.0275 | 25.03 | 4.83 |

TABLE 3-continued

Moisture Sorption/Desorption Data for Form A.

Form A gains a minimal amount of water (0.01%) upon equilibration to 5% RH. The material gained a total of only about 0.03% in the region from 5 to 95% RH, indicating that the material is not hygroscopic. A small amount of hysteresis exists between the hydration and dehydration curves. The characterization data obtained for Form A show that it is a crystalline, unsolvated material, which is not hygroscopic and melts at about 278° C.

C. Form B polymorph of 9-nitrocamptothecin

Form B polymorph of 9-nitrocamptothecin may be made by crystallizing 9-nitrocamptothecin from reagent or HPLC grade acetone or dichloromethane. For example, a saturated or near saturated solution of 9-nitrocamptothecin in acetone or dichloromethane is prepared. The saturated or near saturated solution of 9-nitrocamptothecin in acetone or dichloromethane is then crystallized from solution employing conventional methods for crystallizing organic compounds from organic solvents.

Figure 5:
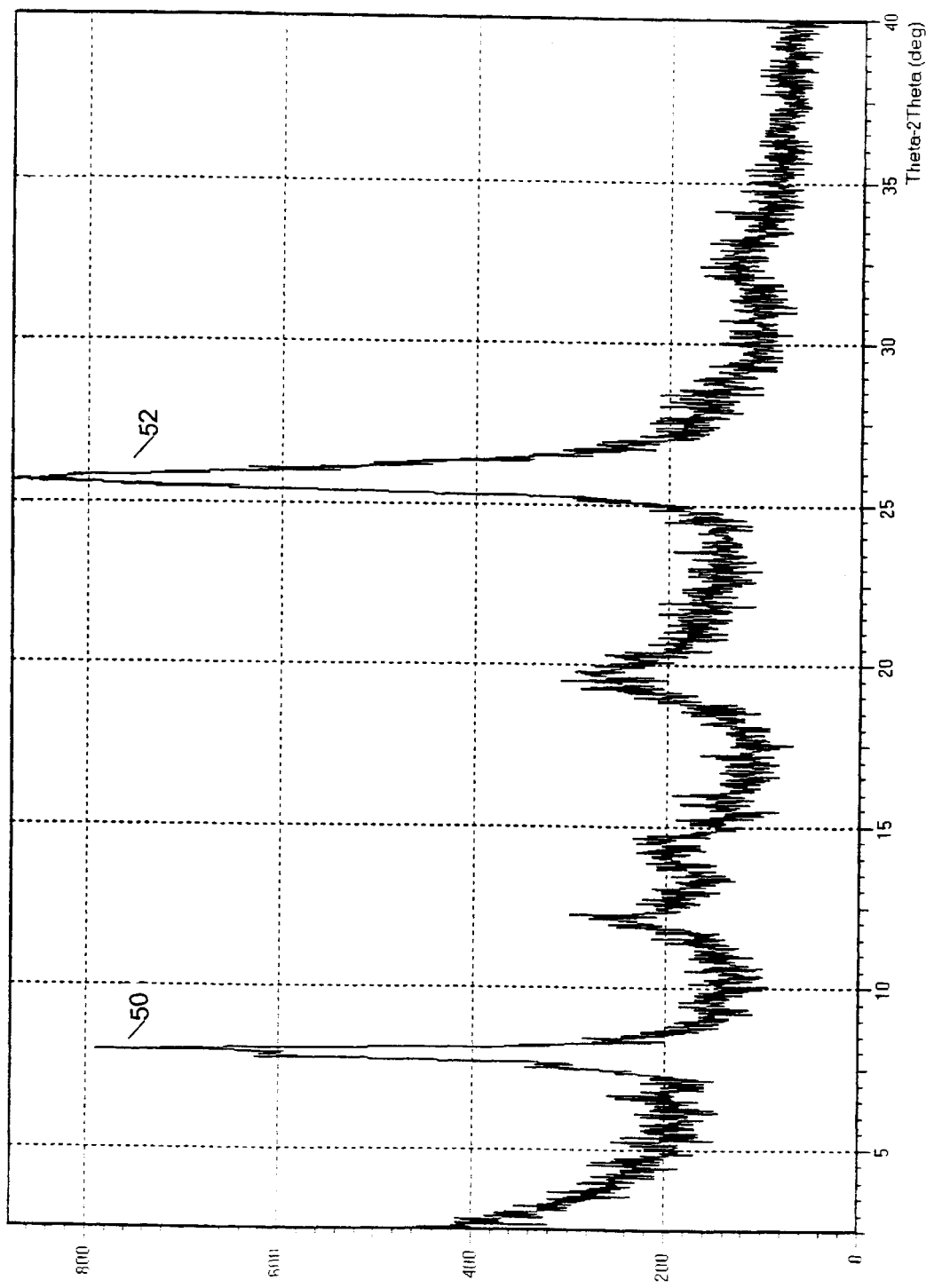
FIG. 5 is a plot of the XRPD pattern of Form B.

The XRPD pattern of Form B is provided in FIG. 5. The XRPD pattern of Form B has two major diffraction lines 50 and 52 at about 8.0 and 25.7 °2θ respectively. There are also several additional broad, weak lines. The XRPD pattern tends to indicate that Form B is not highly crystalline.

An XRPD pattern was also obtained from a sample of Form B that was kept in a closed vial for 31 days at ambient conditions, which pattern did not differ from FIG. 5, indicating the Form B crystalline polymorph is relatively stable. The remaining characterization data, discussed below, suggest that this Form B is a hemihydrate of 9-nitrocamptothecin.

Figure 6:
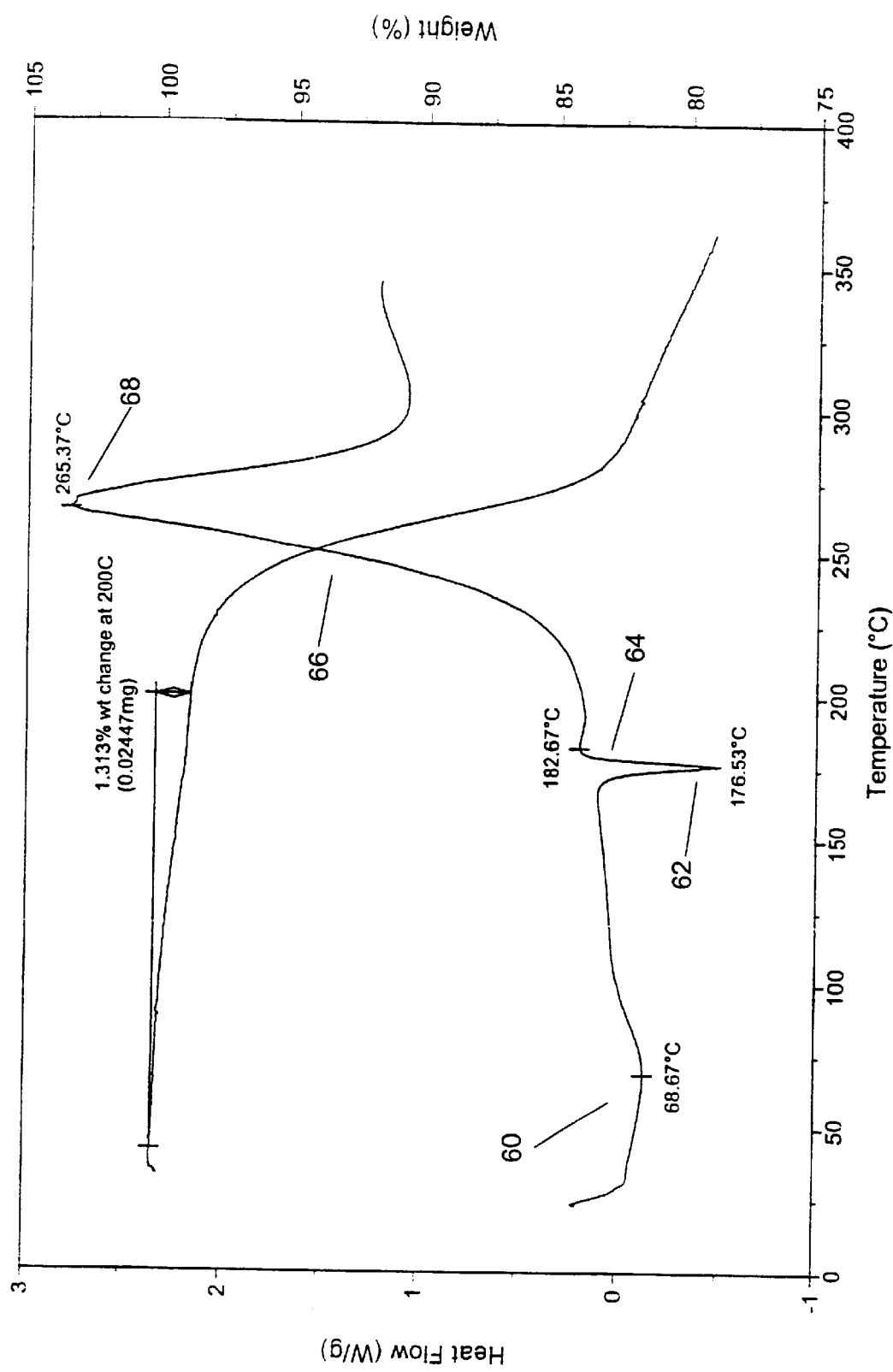
FIG. 6 is a plot of the TGA data and the DSC data for Form B.

Thermogravimetric and DSC data on Form B are provided in Table 4 and plotted in FIG. 6.

TABLE 4

Thermal Data on Crystal Form B

| Form | DSC Results* | TGA Results** |
|---|---|---|
| B | endo 68.7, 176.5 exo 182.7, 265.4 | 1.3 |

*endo - endotherm, exo - exotherm, maximum temperature reported for transition
**percent weight change from 35 to 200° C.

The data show a gradual weight loss of 1.3% out to 200° C. with decomposition occurring above 225° C. The result of a Karl Fischer water analysis for Form B was 2.66%. This tends to demonstrate that Form B contains approximately 2.7% water by weight, and is thus hydrated. Any difference between the TGA and the Karl Fischer analysis may be due to water loss while the sample was equilibrating at 35° C. at the start of the TGA experiment. The theoretical amount for a monohydrate would be approximately 4.4%. Based on the Karl Fischer data, it appears that Form B is a hemihydrate.

The DSC curve for Form B is provided in FIG. 6. It shows a broad endotherm 60 at 68.7° C., assigned to loss of water. This is followed by a sharp endotherm 62 at 176.5° C. and an exotherm 64 at 182.7° C., assigned to a possible melt/ recrystallization. The hot stage microscopy data are summarized in Table 5.

TABLE 5

Hot Stage Microscopy Observations

| Form | Sample # | Observations |
|---|---|---|
| B | 1 | Needles, melt onset 262° C., melt with bubbles at 266° C., solid does not recrystallize. |

The hot stage microscopy data indicates a change in birefringence at 159° C., but a clear melt/recrystallization was not observed under these conditions. The hot stage also showed a melt onset at 200° C. This was not clearly observed in the DSC, which shows a broad exotherm 66 with a maximum 68 at 265.4° C., and is probably due to energetic decomposition observed in this temperature range.

Figure 7:
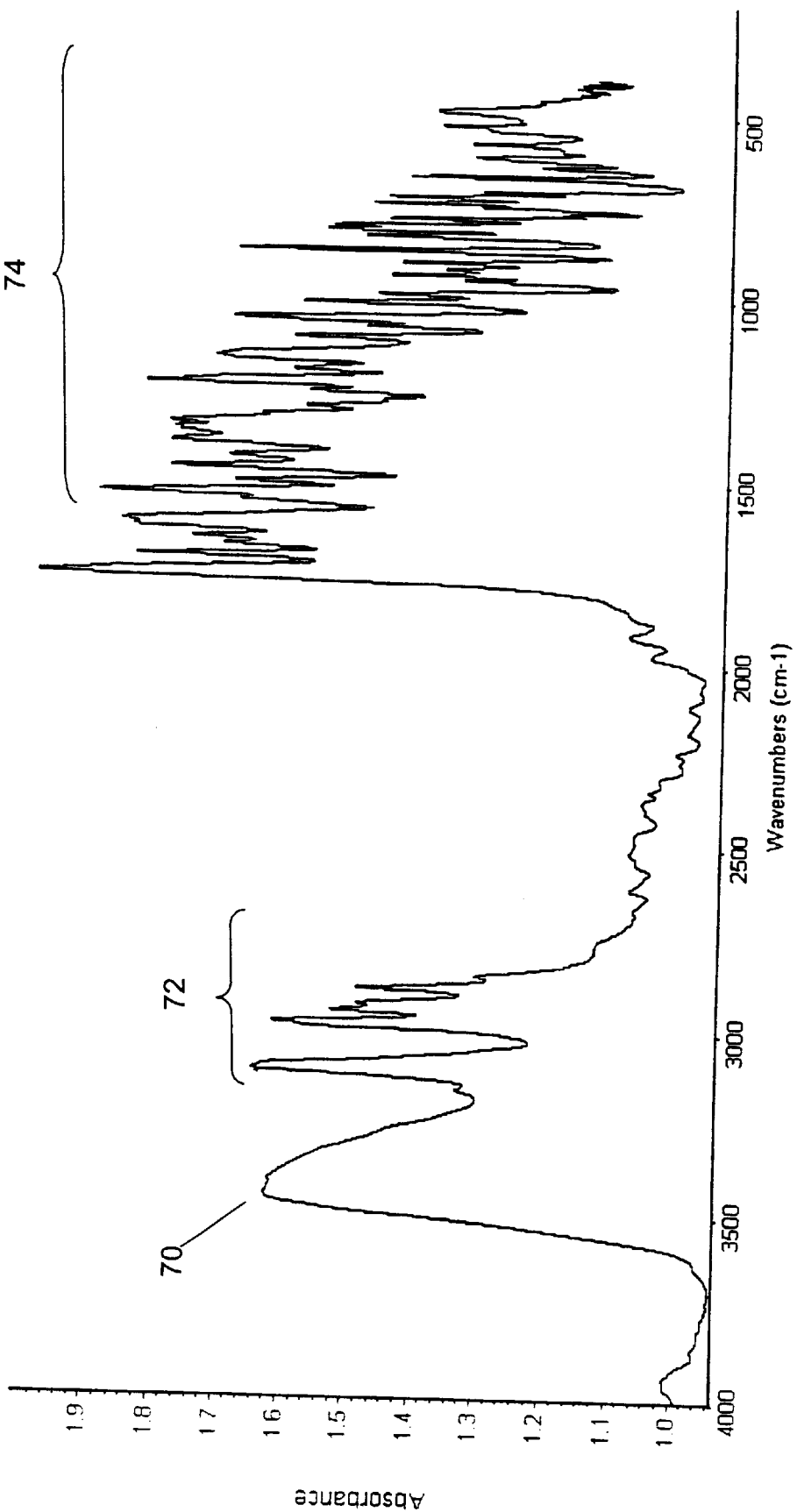
FIG. 7 is a plot of the IR absorption spectrum for Form B.

The IR spectrum for Form B is provided in FIG. 7. The IR spectrum demonstrates a relatively broad OH stretch 70 around 3400 cm$^{-1}$. The aromatic and aliphatic CH stretches 72 between 3100 and 2800 cm$^{-1}$ are broadened compared to the stretches for Form A, as well as the complex fingerprint region 74 from 1700–400 cm$^{-1}$, which includes at least one new absorbance at 1710 cm$^{-1}$.

Figure 8:
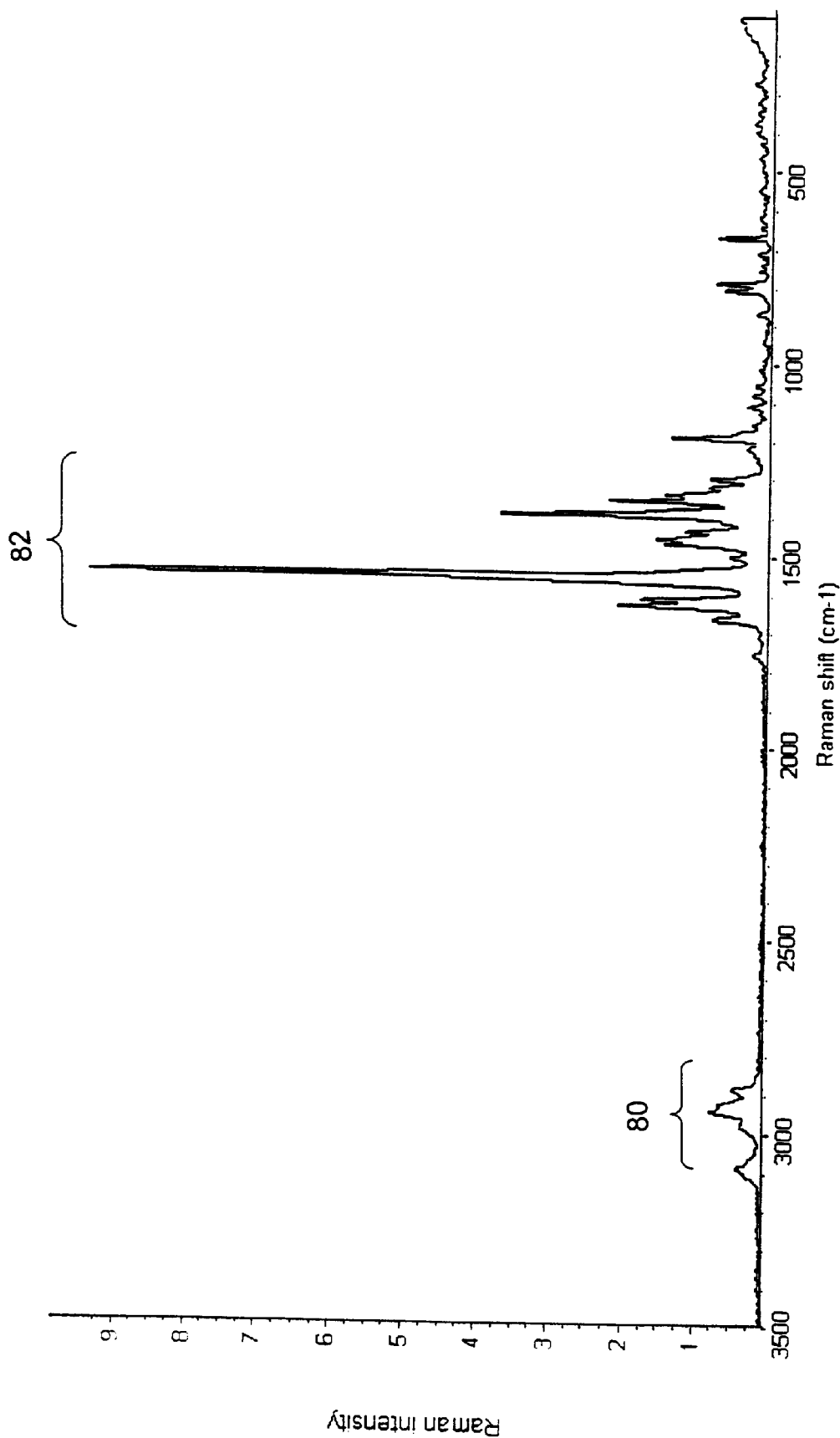
FIG. 8 is a plot of the Raman absorption spectrum for Form B.

The Raman spectrum for Form B is provided in FIG. 8. The Raman spectrum shows relatively weak aromatic and aliphatic CH stretches 80 between 3100 and 2900 cm$^{-1}$, and stronger bands 82 in the region from 1700–1200 cm$^{-1}$.

Moisture sorption/desorption data for Form B is provided below in Table 6.

TABLE 6

Moisture Sorption/Desorption Data for Form B.

| Elap Time Min | Weight Mg | Weight % chg | Samp Temp deg C. | Samp RH % |
|---|---|---|---|---|
| 0.0 | 1.3612 | 0.0000 | 25.03 | 9.87 |
| 27.0 | 1.3478 | −0.9820 | 25.04 | 5.27 |
| 48.0 | 1.3545 | −0.4898 | 25.04 | 14.99 |
| 66.0 | 1.3596 | −0.1151 | 25.04 | 24.85 |
| 79.3 | 1.3636 | 0.1788 | 25.04 | 35.10 |
| 91.3 | 1.3670 | 0.4286 | 25.04 | 45.00 |
| 102.9 | 1.3699 | 0.6416 | 25.04 | 54.97 |
| 115.8 | 1.3725 | 0.8314 | 25.04 | 64.84 |
| 129.0 | 1.3746 | 0.9869 | 25.04 | 74.71 |
| 142.1 | 1.3763 | 1.1118 | 25.04 | 84.56 |
| 158.8 | 1.3779 | 1.2293 | 25.04 | 94.72 |
| 167.2 | 1.3771 | 1.1706 | 25.04 | 85.04 |
| 182.0 | 1.3752 | 1.0310 | 25.03 | 75.38 |
| 195.4 | 1.3727 | 0.8473 | 25.03 | 64.98 |
| 209.1 | 1.3702 | 0.6637 | 25.04 | 55.12 |
| 222.0 | 1.3671 | 0.4359 | 25.04 | 45.03 |
| 235.1 | 1.3637 | 0.1861 | 25.04 | 34.99 |
| 269.0 | 1.3596 | −0.1151 | 25.04 | 24.89 |
| 295.8 | 1.3542 | −0.5118 | 25.04 | 14.94 |
| 321.7 | 1.3470 | −1.0408 | 25.04 | 5.00 |

This data indicates that Form B lost a significant amount of water (0.98%) upon equilibration at 5% RH. The material then gained a total of 2.21% in the region from 5 to 95% RH, indicating that the material is relatively hygroscopic. There is essentially no hysterisis between the hydration and dehydration curves. Based on the characterization data, Form B appears to be a hemihydrate of 9-nitrocamptothecin, which can gain or lose water with minimal change in the crystal form.

D. Form C polymorph of 9-nitrocamptothecin

Form C polymorph of 9-nitrocamptothecin may be made by crystallizing 9-nitrocamptothecin from reagent or HPLC grade tetrahydrofuran. For example, a saturated or near saturated solution of 9-nitrocamptothecin in tetrahydrofuran is prepared. The saturated or near saturated solution of 9-nitrocamptothecin in tetrahydrofuran is then crystallized from solution employing conventional methods for crystallizing organic compounds from organic solvents.

Figure 9:
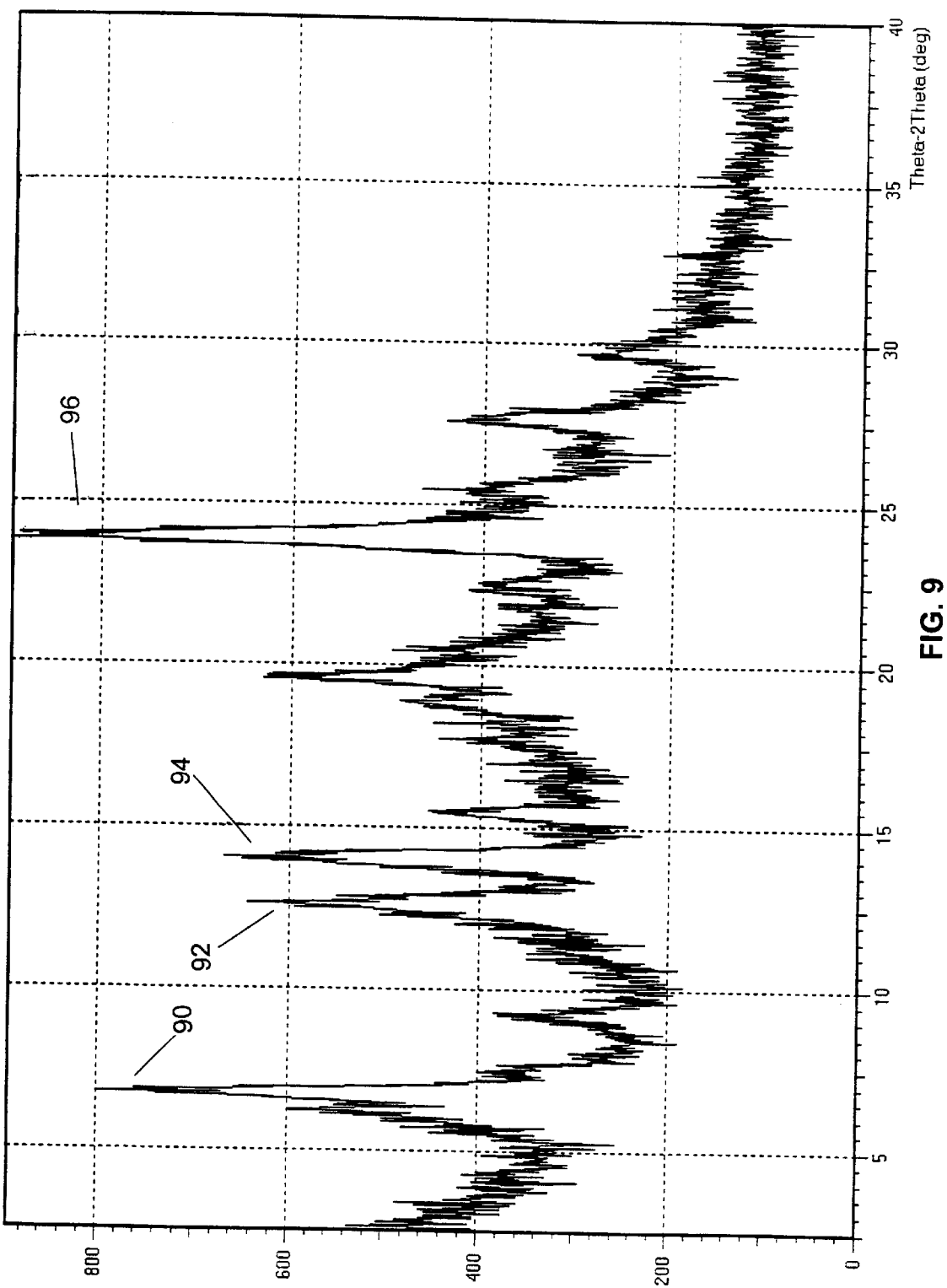
FIG. 9 is a plot of the XRPD pattern of Form C.

The XRPD pattern of Form C is provided in FIG. 9. The Form C pattern has major diffraction lines 90, 92, 94, 96 at about 6.7, 12.5, 14.0 and 23.9 °2θ respectively. The XRPD pattern indicates that the material is not highly crystalline and may contain some amorphous material. This pattern was only obtained on samples generated from tetrahydrofuran.

TGA data on Form C are provided below in Table 7.

TABLE 7

Thermal Data on Crystal Form C

| Form | DSC Results* | TGA Results** |
|---|---|---|
| C | exo 134.1, 156.5, 274.6 | 15.7 |

*endo - endotherm, exo - exotherm, maximum temperature reported for transition
**percent weight change from 35 to 200° C.

The data show a weight loss of 15.7% below 200° C. with decomposition occurring above 250° C. This is comparable to the theoretical amount (15.5%) for a mono THF solvate. The characterization of this weight loss as THF solvent is supported by the $^1$H NMR data. An attempt to desolvate this form under vacuum, indicated this form becomes amorphous under these conditions.

Figure 10:
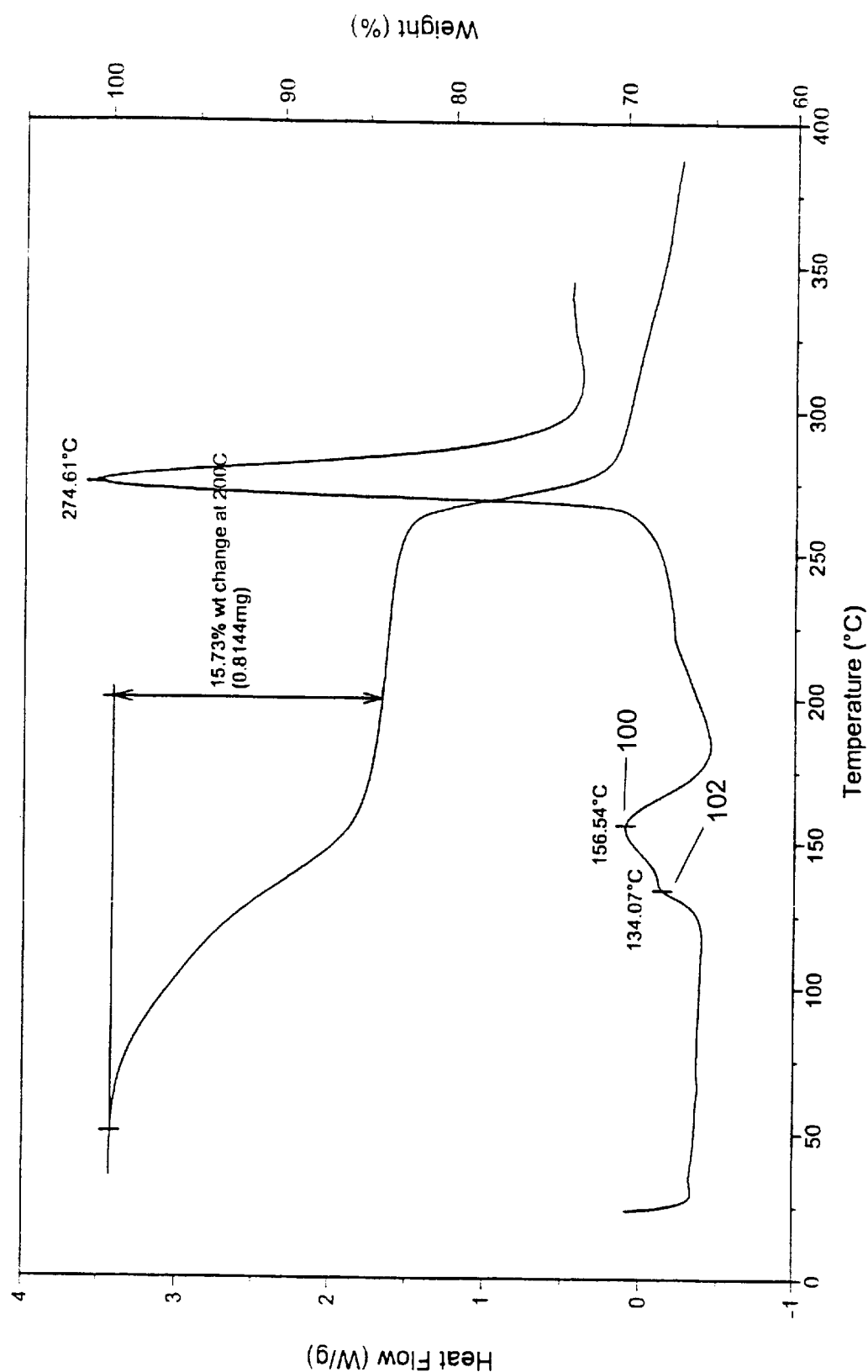
FIG. 10 is a plot of the TGA data and the DSC data for Form C.

Thermogravimetric and DSC data for Form C is plotted in FIG. 10. No clear endothermic transitions corresponding to loss of solvent or water are observed. However, a broad exotherm 100 at 156.5° C. is observed with a shoulder 102 at 134.1° C. Based on hot stage microscopy, this may correspond to a recrystallization which occurs as the solvent leaves. Again, a melt (endotherm) is not observed prior to the decomposition exotherm at 274.6° C., however, a melt is evident by hot stage microscopy. This indicates that the melt endotherm is not evident by DSC due to it's being marked by the highly energetic decomposition. Hot stage microscopy results are summarized below in Table 8.

TABLE 8

Hot Stage Microscopy Observations for Form C

| Form | Sample # | Observations |
|---|---|---|
| C | 1 | Opaque solids, small solids melt at 126° C., melt onset 246° C., melt at 263° C. |

Figure 11:
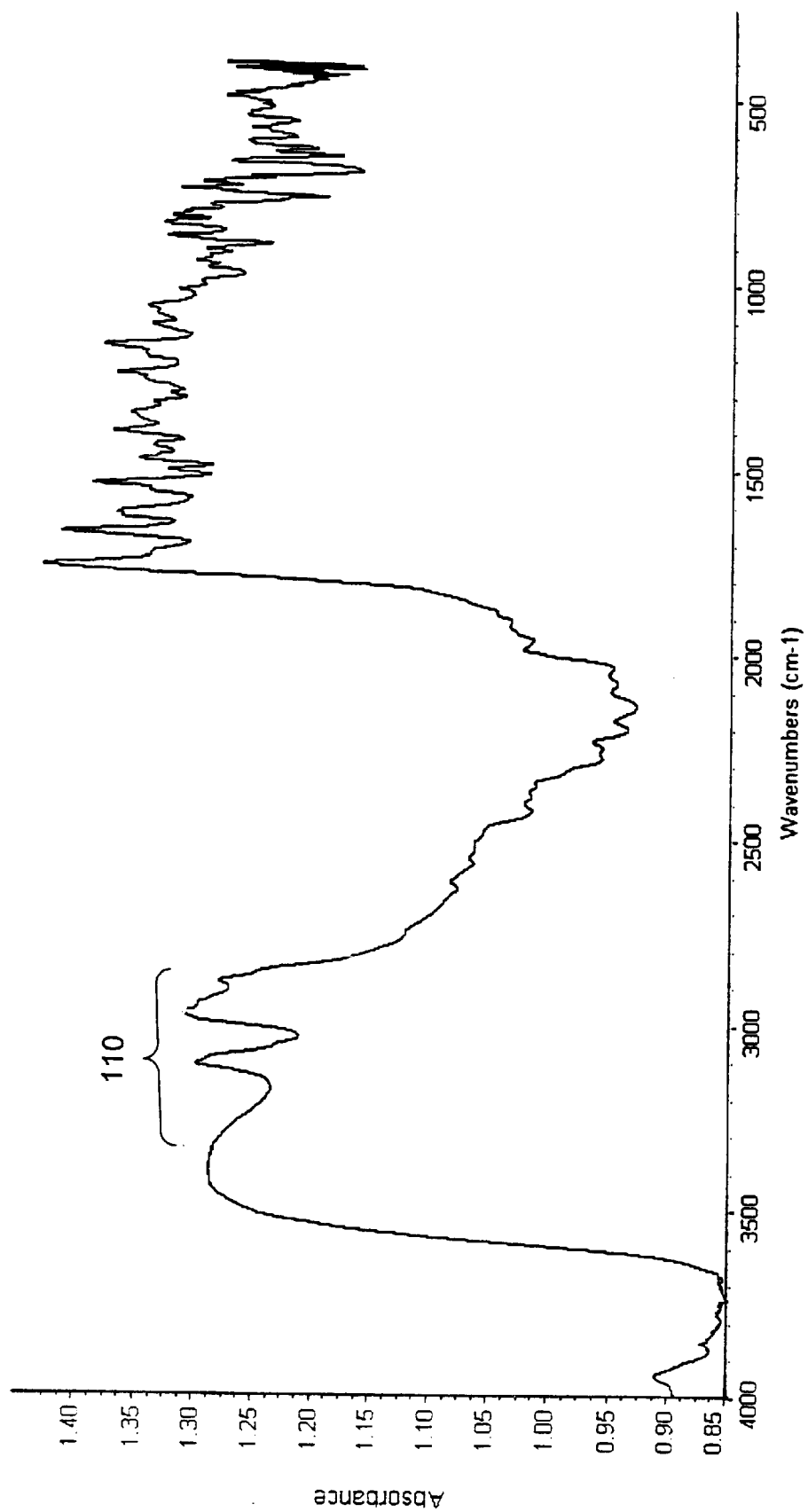
FIG. 11 is a plot of the IR absorption spectrum for Form C.
Figure 12:
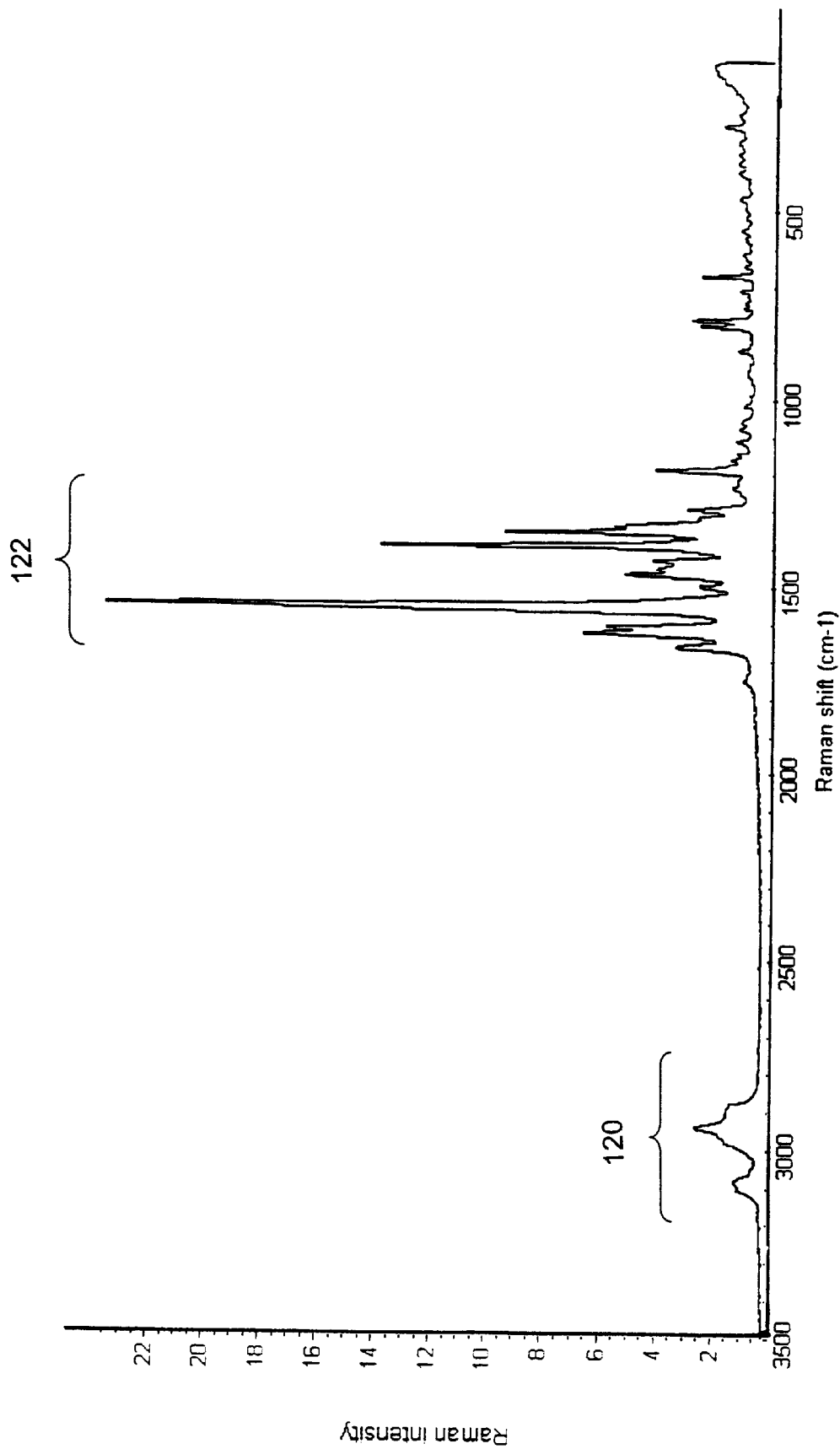
FIG. 12 is a plot of the Raman absorption spectrum for Form C.

The IR spectrum for Form C is provided in FIG. 11. The IR data collected on this form show an extremely broad OH stretch 110 around 3400 cm$^{-1}$. No clear absorption bands due to THF can be assigned. Although the peak positions generally correspond with those of Form A, all the peaks in the entire spectrum have broadened significantly. The Raman spectrum for Form C is provided in FIG. 12. The Raman spectrum shows relatively weak aromatic and aliphatic CH stretches 120 between 3100 and 2800 cm$^{-1}$, and stronger bands 122 in the region from 1700–1300 cm$^{-1}$.

The result of a Karl Fischer water analysis was 1.06%. These results indicate that Form C contains approximately 1.1% water by weight, which may be associated with the amorphous portion of the sample. Based on the characterization data, Form C appears to be a poorly crystalline THF solvate, which desolvates to a mainly amorphous material.

E. Form D polymorph of 9-nitrocamptothecin

Form D polymorph of 9-nitrocamptothecin may be made by crystallizing 9-nitrocamptothecin from reagent or HPLC grade acetonitrile. For example, a saturated or near saturated solution of 9-nitrocamptothecin in acetonitrile is prepared. The saturated or near saturated solution of 9-nitrocamptothecin in acetonitrile is then crystallized from solution employing conventional methods for crystallizing organic compounds from organic solvents.

Figure 13:
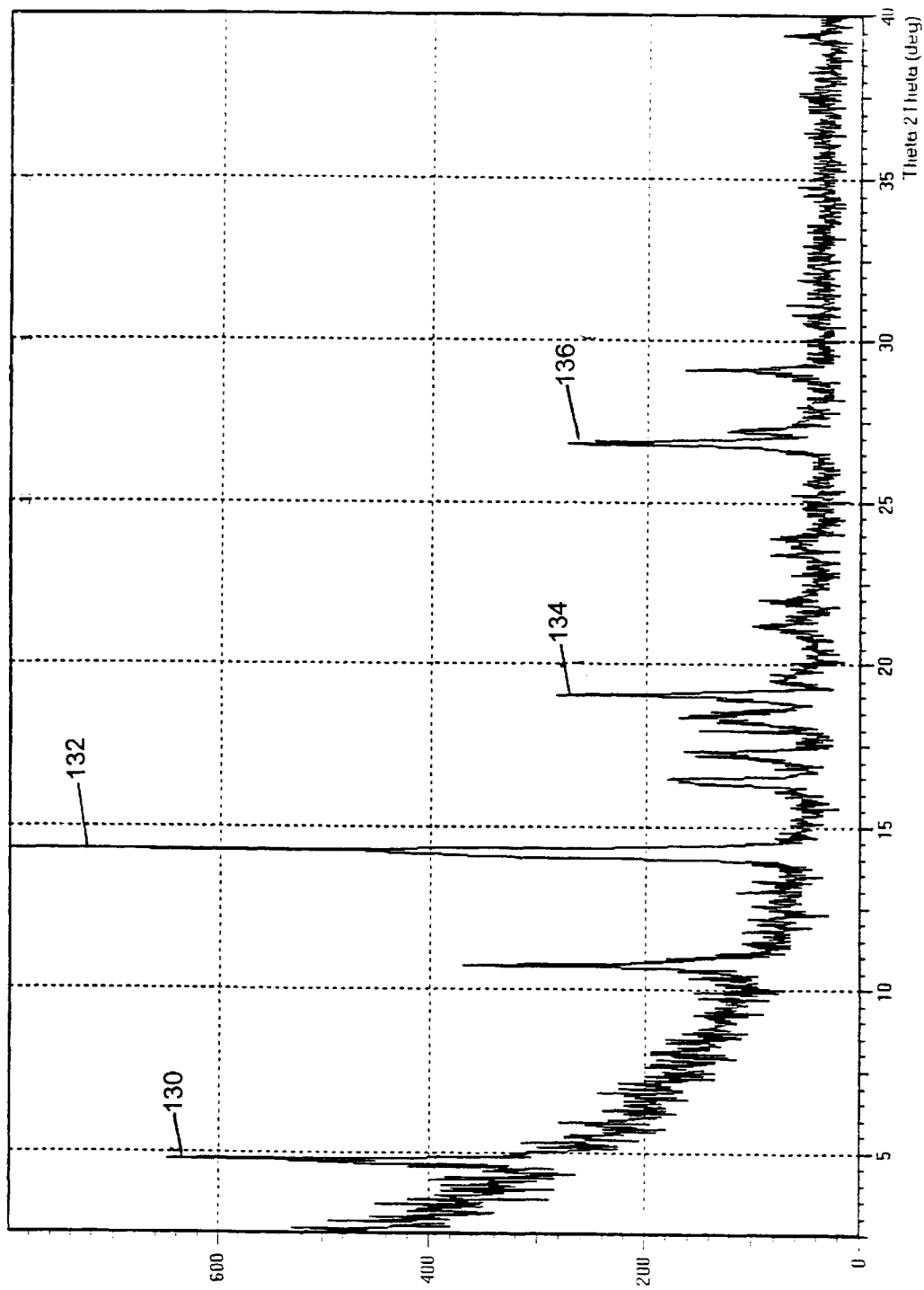
FIG. 13 is a plot of the XRPD pattern of Form D.

The XRPD pattern of Form D is provided in FIG. 13. The Form D pattern has major diffraction lines 130, 132, 134, 136 at about 4.8, 14.2, 19.1 and 26.8 °2θ respectively. Several additional broad, weak lines are observed as well. This pattern was only obtained from material in contact with acetonitrile.

TGA data on Form D are summarized below in Table 9.

TABLE 9

Thermal Data on Crystal Form D

| Form | DSC Results* | TGA Results** |
|---|---|---|
| D | Endo 177.6, 274.9<br>exo 201.2, 280.3 | 8.7 |

*endo - endotherm, exo - exotherm, maximum temperature reported for transition
**percent weight change from 35 to 200° C.

This data shows a weight loss of 8.7% below 200° C. with decomposition occurring above 250° C. This is comparable to the theoretical amount (9.4%) for a mono acetonitrile solvate. A Karl Fischer water analysis indicates form D contains less than 0.9% water by weight. These data confirm that the TGA observed weight loss is due to acetonitrile.

Figure 14:
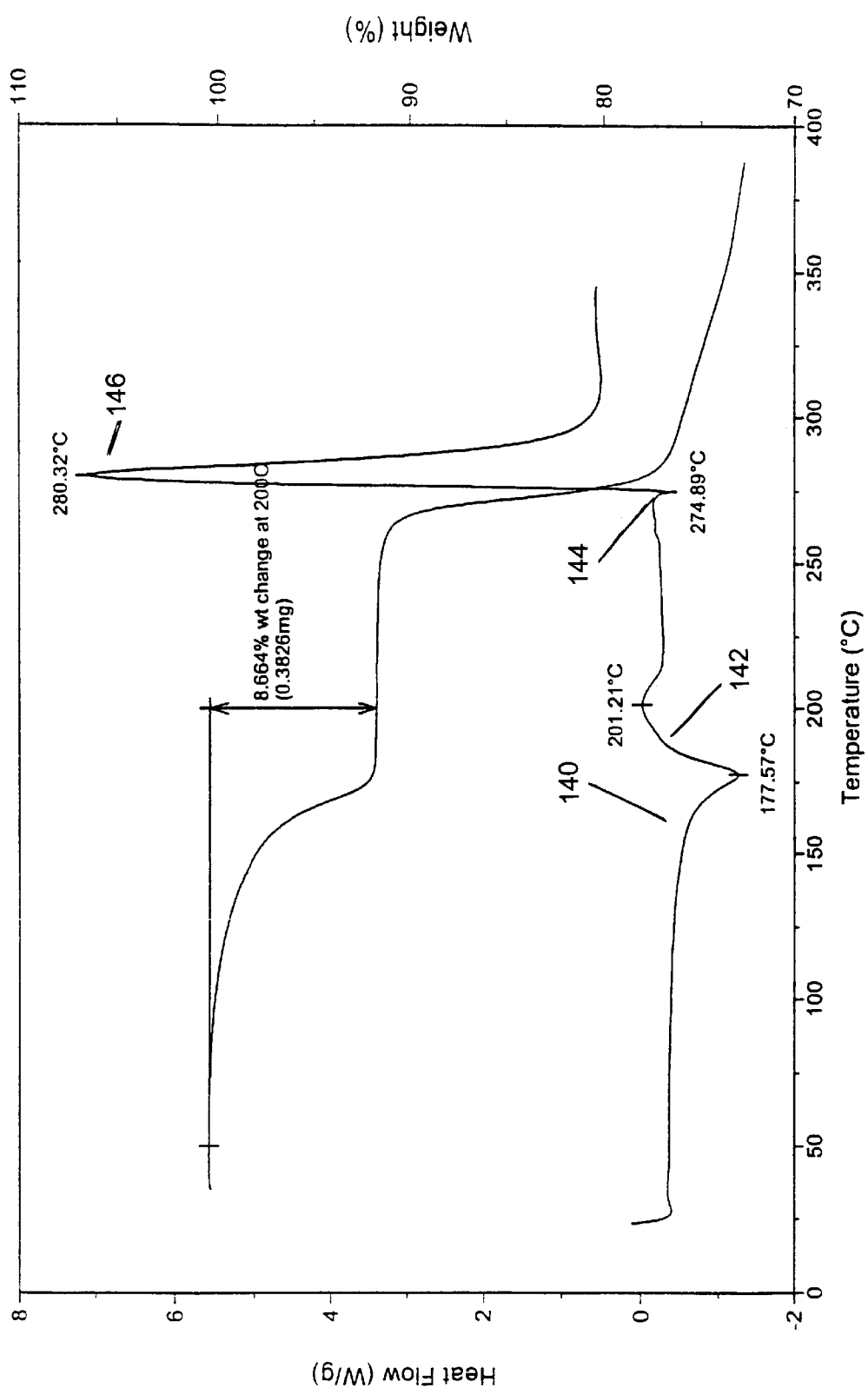
FIG. 14 is a plot of the TGA data and the DSC data for Form D.

The DSC curve for Form D is provided in FIG. 14. It shows a broad endothermic transition 140 corresponding to loss of solvent at 177.6° C. This is consistent with the hot stage data, summarized in Table 10 below, which illustrated solids darkening at 183° C.

TABLE 10

Hot Stage Microscopy Observations for Form D

| Form | Sample # | Observations |
|---|---|---|
| D | 1 | Plates, lose birefringence at 180° C., some recrystallization at 241° C., melt onset 262° C. |

Making reference now to FIG. 14, the broad endothermic transition 140 is followed by a broad exotherm 142 at 201.2° C. This likely corresponds to a recrystallization, which occurs as the solvent leaves and would be consistent with the hot stage observation at 244° C. of small needles growing. A small melt endotherm 144 is observed at 274.9° C., just prior to the decomposition exotherm 146 at 280.3° C., whereas the melt onset is observed at 262° C. by hot stage microscopy.

Figure 15:
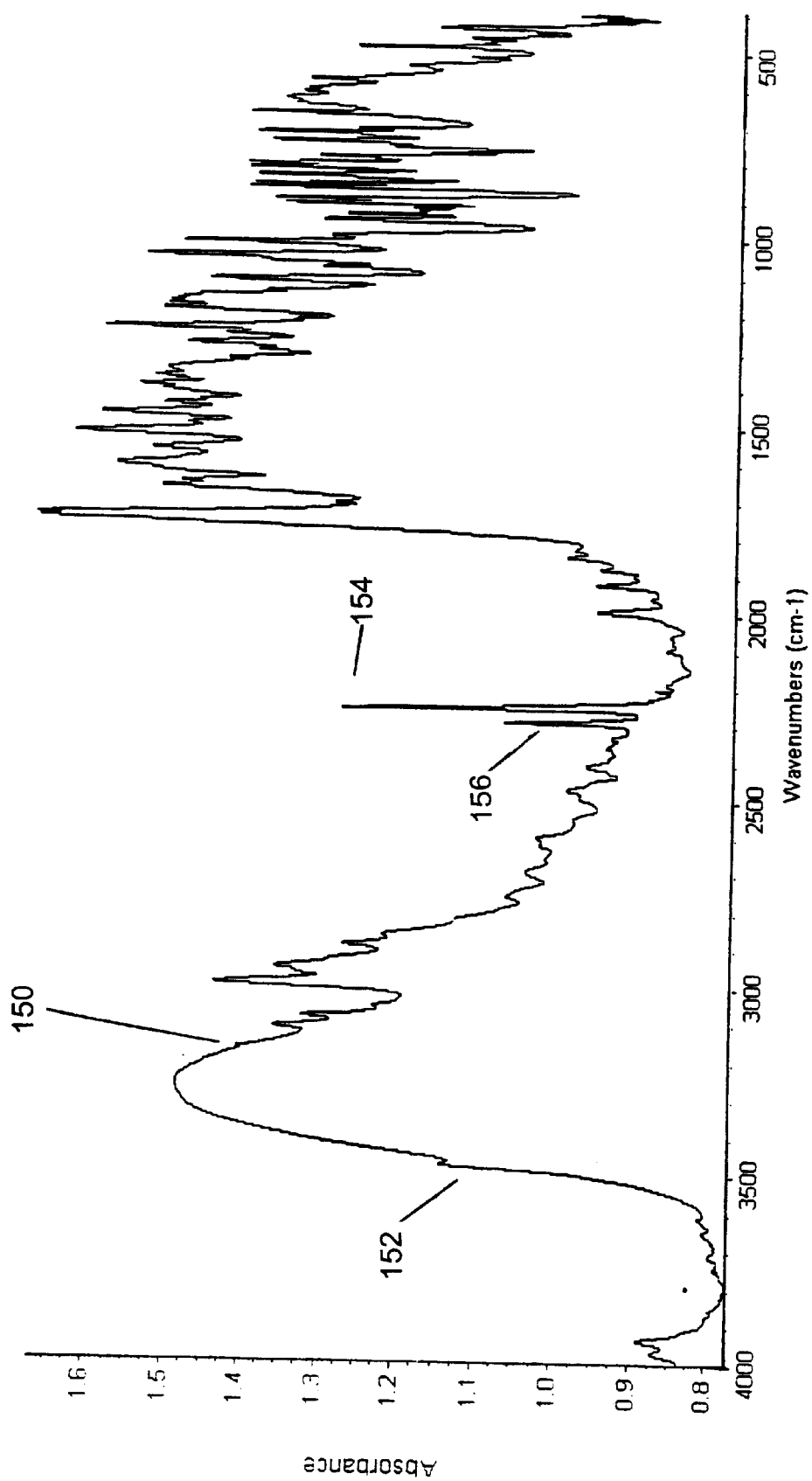
FIG. 15 is a plot of the IR absorption spectrum for Form D.

The IR spectrum is plotted in FIG. 15. The IR data on Form D show an extremely broad OH stretch 150 shifted to around 3265 cm$^{-1}$ and a smaller sharp resonance 152 around 3470 cm$^{-1}$. Two sharp resonances 154 and 156 are observed for the acetonitrile CN stretch at 2253 and 2290 cm$^{-1}$. All the peaks in the entire spectrum have broadened significantly from that of Form A.

Figure 16:
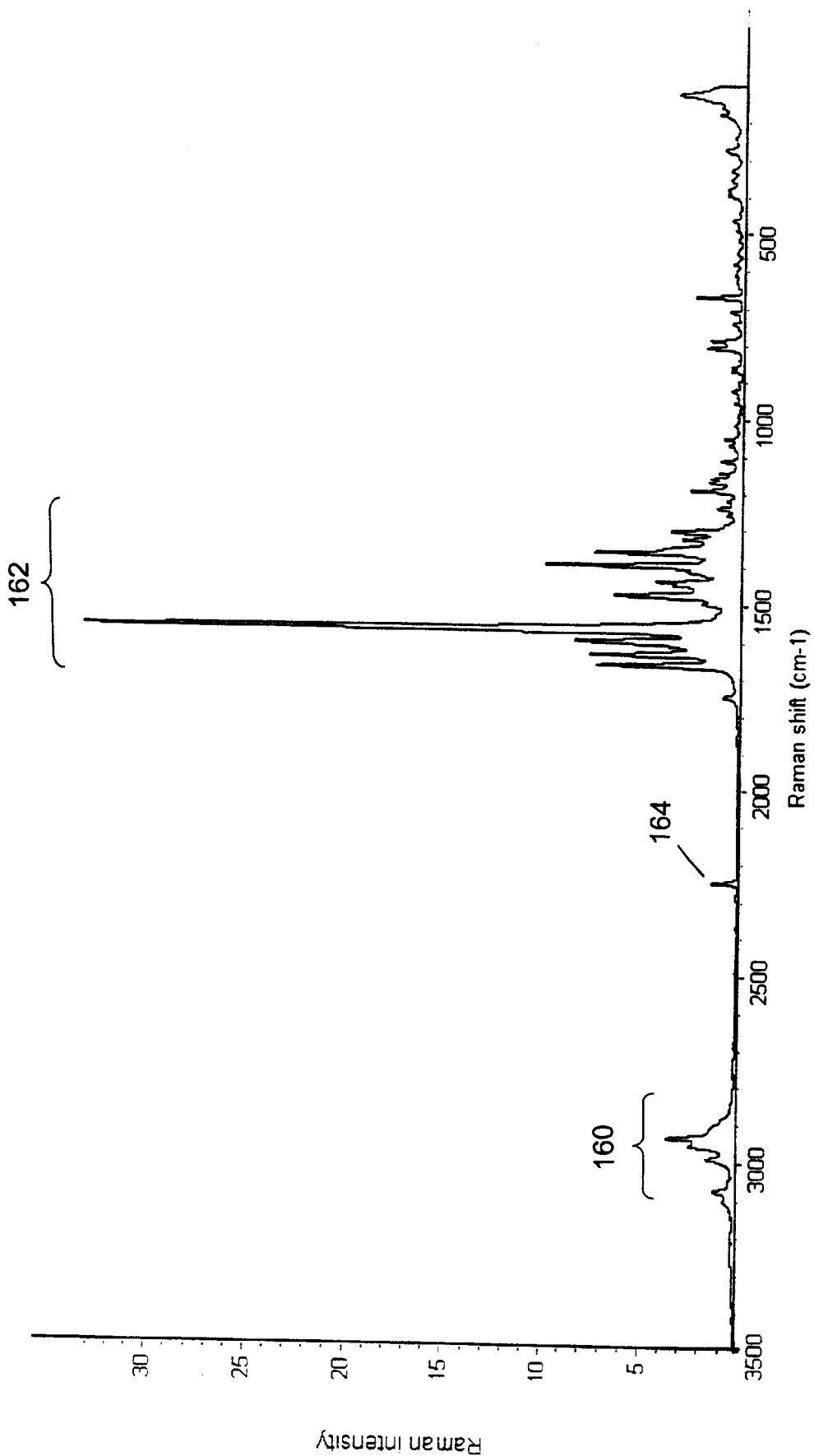
FIG. 16 is a plot of the Raman absorption spectrum for Form D.

The Raman spectrum is plotted in FIG. 16. The Raman spectrum shows relatively weak aromatic and aliphatic CH stretches 160 between 3100 and 2800 cm$^{-1}$, and stronger bands 162 in the region from 1700–1300 cm$^{-1}$. There is also a CN resonance 164 at 2250 cm$^{-1}$. Based on the characterization data, Form D is a crystalline acetonitrile solvate, which may change forms with heating and/or solvent loss.

F. Form E polymorph of 9-nitrocamptothecin

Form E polymorph of 9-nitrocamptothecin may be made by crystallizing 9-nitrocamptothecin from reagent or HPLC grade chloroform. For example, a saturated or near saturated solution of 9-nitrocamptothecin in chloroform is prepared. The saturated or near saturated solution of 9-nitrocamptothecin in chloroform is then crystallized from solution employing conventional methods for crystallizing organic compounds from organic solvents.

Figure 17:
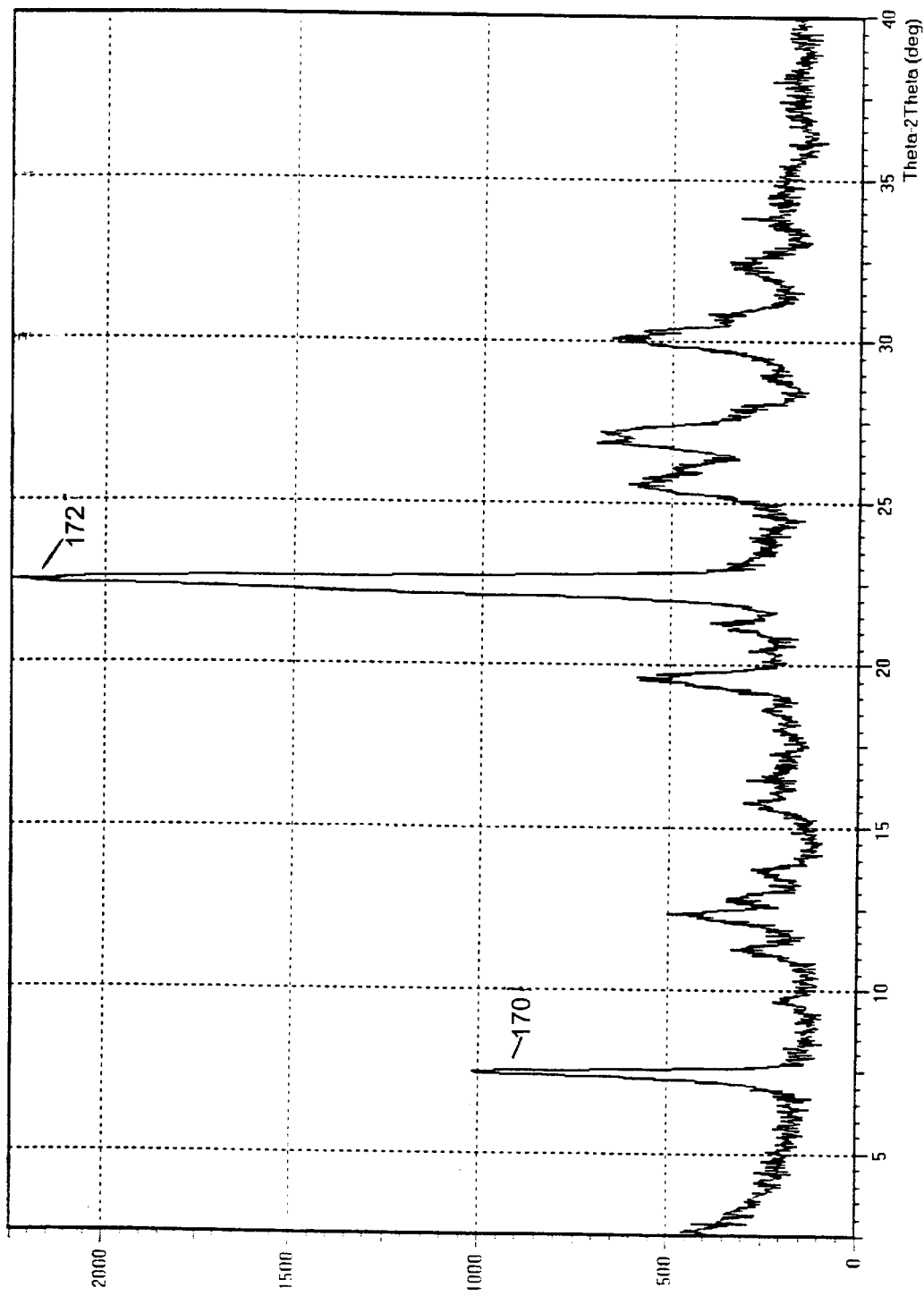
FIG. 17 is a plot of the XRPD pattern of Form E.

The XRPD pattern of Form E is provided in FIG. 17. It has major diffraction lines 170 and 172 at about 7.4 and 22.5 °2θ respectively. Some of the XRPD patterns obtained on Form E show additional broad lines at 8.1 and 20.9 °2θ. These additional lines may be due to preferred orientation effects. The XRPD pattern was only obtained from chloroform and indicates that the material is not highly crystalline.

TGA data on Form E is summarized below in Table 11. It shows a weight loss of 8.5% below 200° C. with decomposition occurring above 250° C. This corresponds to approximately 0.3 mole of chloroform per mole of 9-nitrocamptothecin whereas the theoretical amount for a single equivalent of chloroform solvent is 23.3%.

TABLE 11

Thermal Data on Crystal Form E

| Form | DSC Results* | TGA Results** |
|---|---|---|
| E | Endo 276.2<br>exo 181.6, 200.9, 281.9 | 8.5 |

*endo - endotherm, exo - exotherm, maximum temperature reported for transition
**percent weight change from 35 to 200° C.

Results of a Karl Fischer water analysis were less than 0.67%. These results indicate that Form E contains less than approximately 0.7% water by weight. Thus, Form E appears to contain approximately one quarter of a mole, e.g. between one fifth and one third of an equivalent, of chloroform solvent.

Figure 18:
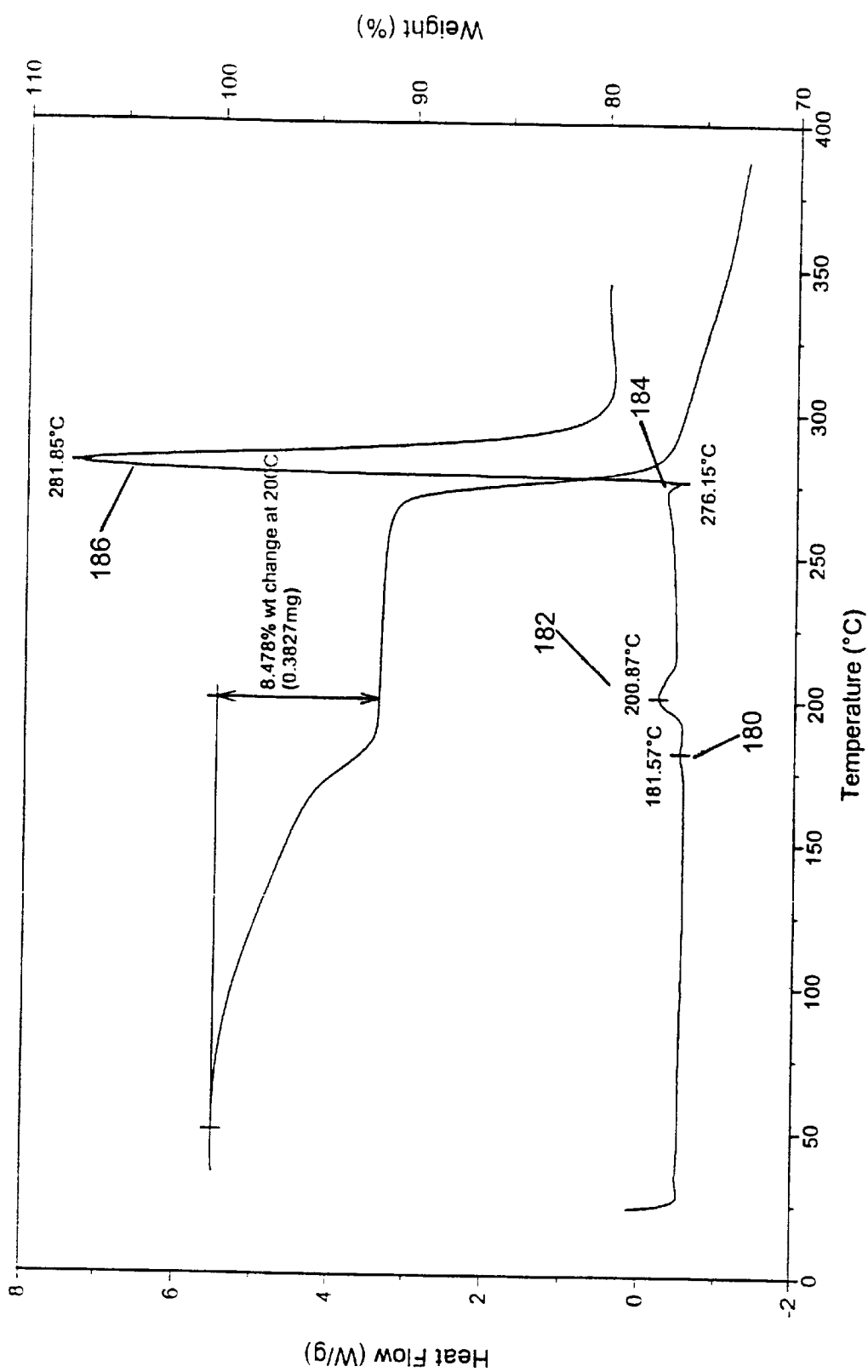
FIG. 18 is a plot of the TGA data and the DSC data for Form E.

The DSC curve is provided in FIG. 18. There are two exothermic transitions, which occur at slightly higher temperatures than that for Form C. No clear endothermic transitions corresponding to loss of solvent or water are observed. However, two broad exotherms 180 and 182 are observed at 181.6° C. and 200.9° C. These transitions may correspond to recrystallizations occuring as the solvent is depleted.

This is consistent with the hot stage microscopy data summarized below in Table 12, which indicate small needles melting at 197° C., then needles growing again at 239° C. In contrast to Form C, a small melt endotherm 184 is observed at 276.2° C., just prior to the sharp decomposition exotherm 186 at 281.9° C. This is supported by the hot stage data, which shows needles finally melting at 265° C.

TABLE 12

Hot Stage Microscopy Observations for Form E

| Form | Sample # | Observations |
|---|---|---|
| E | 1 | Small opaque needles, melt at 194° C., recrystallization at 236° C., melt onset 262° C. |

Figure 19:
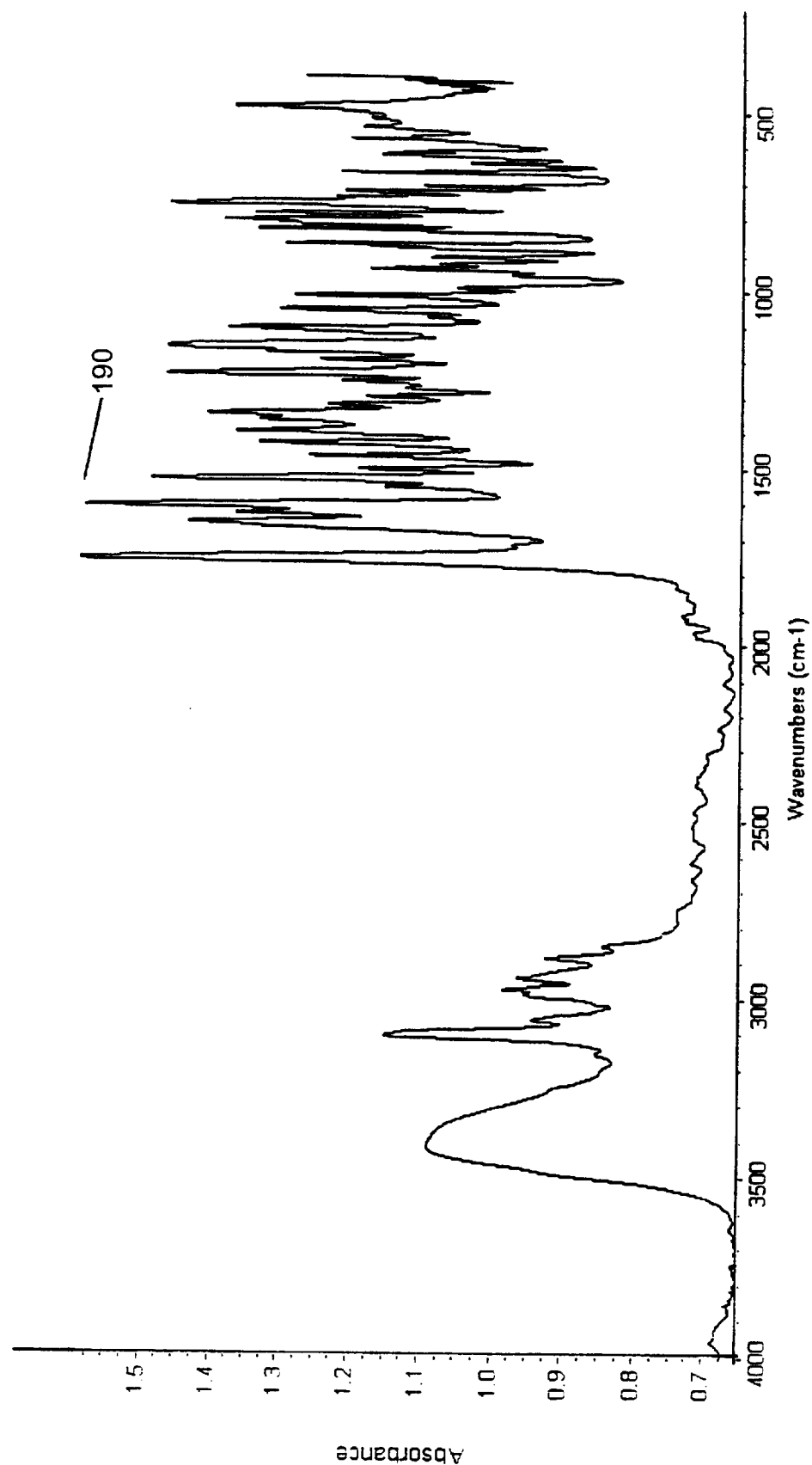
FIG. 19 is a plot of the IR absorption spectrum for Form E.

The IR spectrum for Form E is plotted in FIG. 19. The carbonyl stretch 190 at 1710 cm$^{-1}$ is shifted from that for Form B. No additional peaks due to the chloroform solvent were observed. Although the peak positions generally correspond with those of form A, all the peaks in the entire spectrum have broadened significantly.

Figure 20:
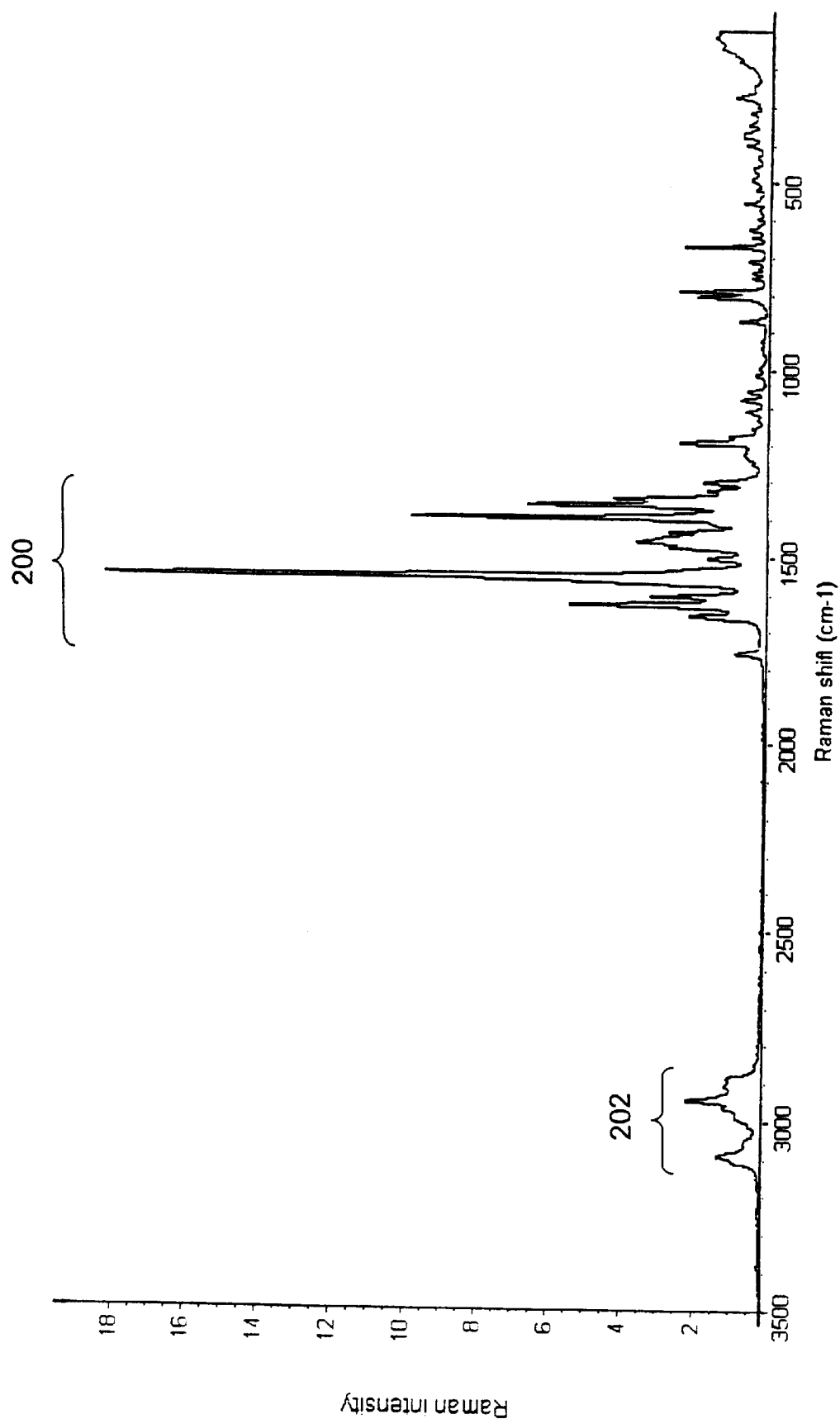
FIG. 20 is a plot of the Raman absorption spectrum for Form E.

The Raman spectrum for Form E is provided in FIG. 20. The Raman spectrum shows relatively weak aromatic and aliphatic CH stretches 200 between 3100 and 2800 cm$^{-1}$, and stronger bands 202 in the region from 1700–1300 cm$^{-1}$. Based on the characterization data, Form E is a poorly crystalline material that may be a one-quarter chloroform solvate.

G. Form F polymorph of 9-nitrocamptothecin

Form F polymorph of 9-nitrocamptothecin may be made by crystallizing 9-nitrocamptothecin from reagent or HPLC grade ethanol, acetone, dichloromethane, tetrahydrofuran or acetonitrile to form an initial crystalline product as described for Forms B, C and D, and recrystallizing the initial crystalline product from a saturated solution of dimethylformamide (DMF) and water (DMF/H2O :: 75%/25%, v/v) that contains excess undissolved material comprising the initial crystalline material. The recrystallization from a saturated solution containing an initital crystalline material is known as an interconversion. The solubility of 9-nitrocamptothecin in DMF/H2O :: 75%/25%, v/v is then determined. A saturated solution of 9-nitrocamnptothecin in DMF/H2O :: 75%/25%, v/v having a visible excess of the initial crystalline material, e.g. a slurry, is then prepared. The saturated solution of 9-nitrocamptothecin in DMF/H2O :: 75%/25%, v/v slurry of the initial crystalline material is then recrystallized (interconverted) from solution. This recrystallization from the slurry is carried out by agitating the slurry for 7 days at ambient temperature using a shaker block or rotating wheel. After the 7-day agitation, insoluble solids are recovered from the slurry by filtration. The recrystallization or interconversion is obtained over a relatively long period of time relative to crystallization of the initial crystalline product. Again, as it is known in the art of growing crystals in general that higher quality crystals are generally favored by conditions that favor slower crystal formation, including those affecting kinetics directly, such as temperature, the recrystallization conditions may be appropriately be adjusted to obtain higher quality crystalline material as necessary. Thus, for example, if poor crystals are formed under an initial set of interconversion conditions, the solvent temperature may be reduced and the agitation period can be decreased relative to the initial set of interconversion conditions.

Figure 21:
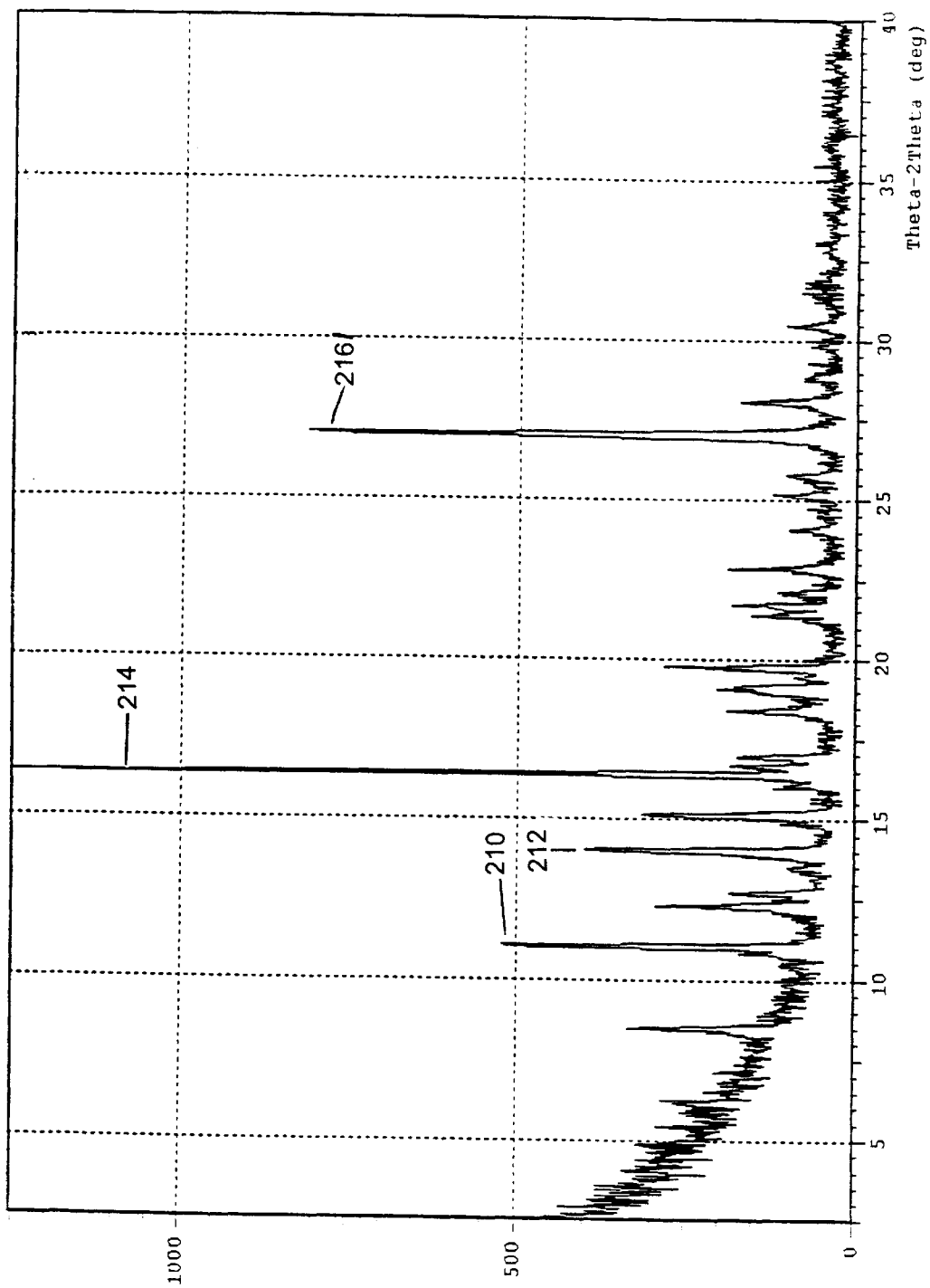
FIG. 21 is a plot of the XRPD pattern of Form F.

The XRPD pattern of Form F is provided in FIG. 21. It has major diffraction lines 210, 212, 214, and 216 at about 11.0, 14.0, 16.4 and 27.0 °2θ respectively. Several additional sharp, but weaker, lines are observed as well. The pattern indicates that the material is relatively highly crystalline. This pattern was obtained from material from an interconversion study using DMF/H$_2$O (75%/25%, v/v) as the solvent.

Figure 22:
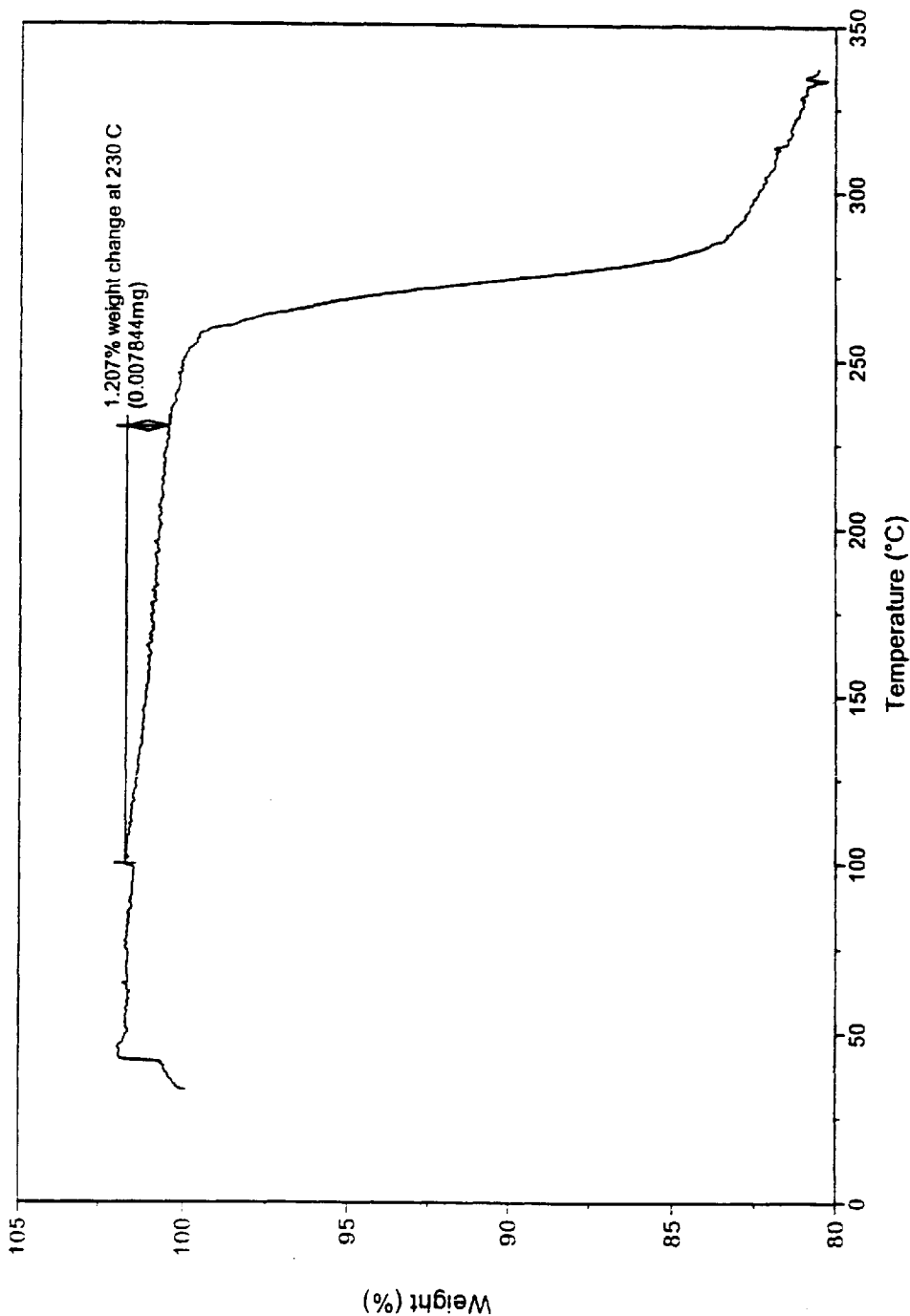
FIG. 22 is a plot of the TGA data for Form F.

TGA data on Form F are summarized below in Table 13 and provided in FIG. 22. The data show a weight loss of only 1.2% between 100 and 230° C., with decomposition occurring above 250° C. Referring to FIG. 22, the TGA curve for Form F is similar to that observed for the hydrated form B. The theoretical amount for a single equivalent of water is approximately 4.4%.

TABLE 13

Thermal Data on Crystal Form F

| Form | TGA Results* |
|---|---|
| F | 1.2 |

*percent weight change from 100 to 230° C.

Figure 23:
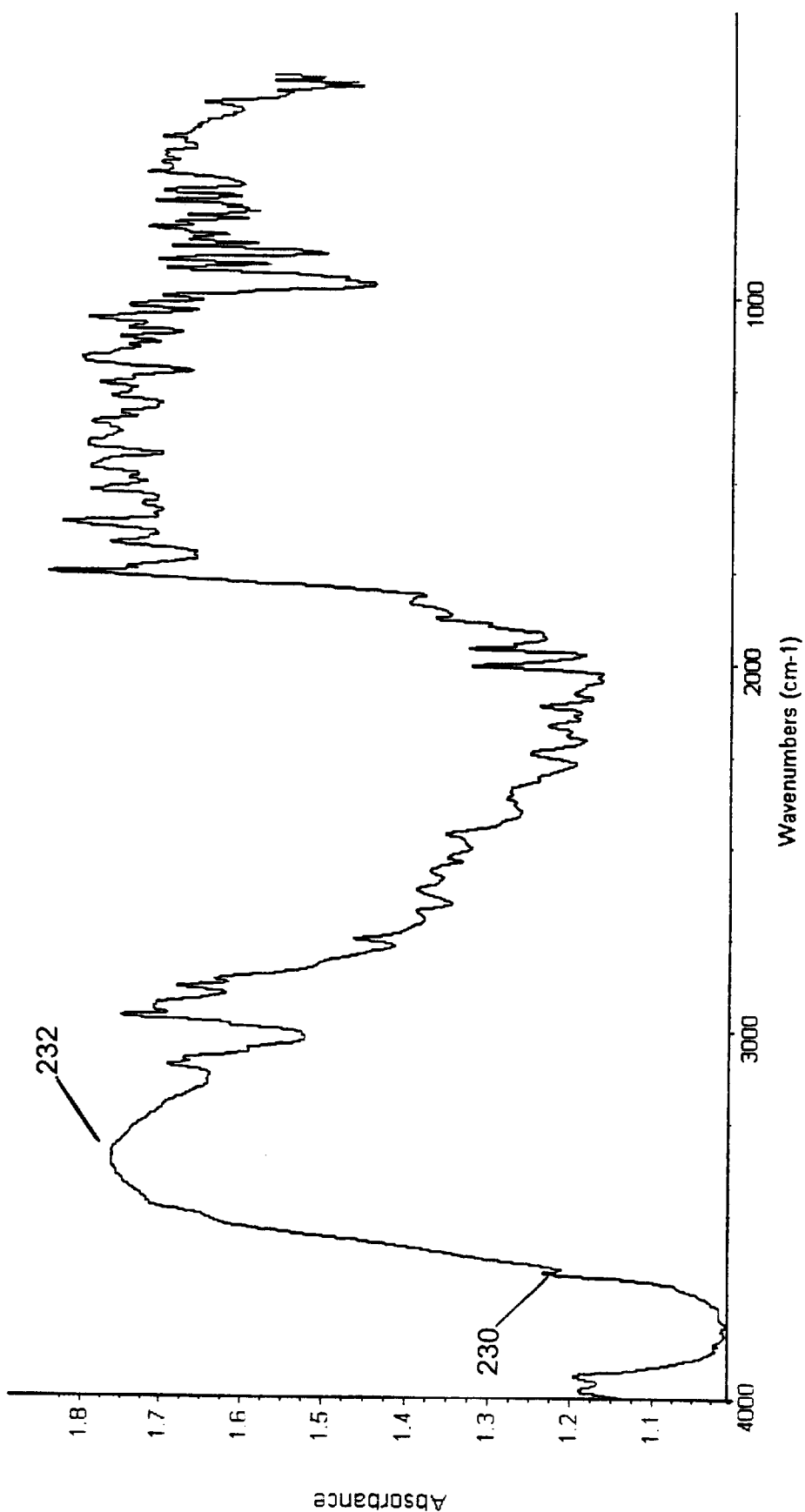
FIG. 23 is a plot of the IR absorption spectrum for Form F.

The IR spectrum for Form F is plotted in FIG. 23. The IR data show an extremely broad OH stretch 230 around 3400 cm$^{-1}$ and a sharp, crystalline OH stretch 232 at 3650 cm$^{-1}$.

Figure 24:
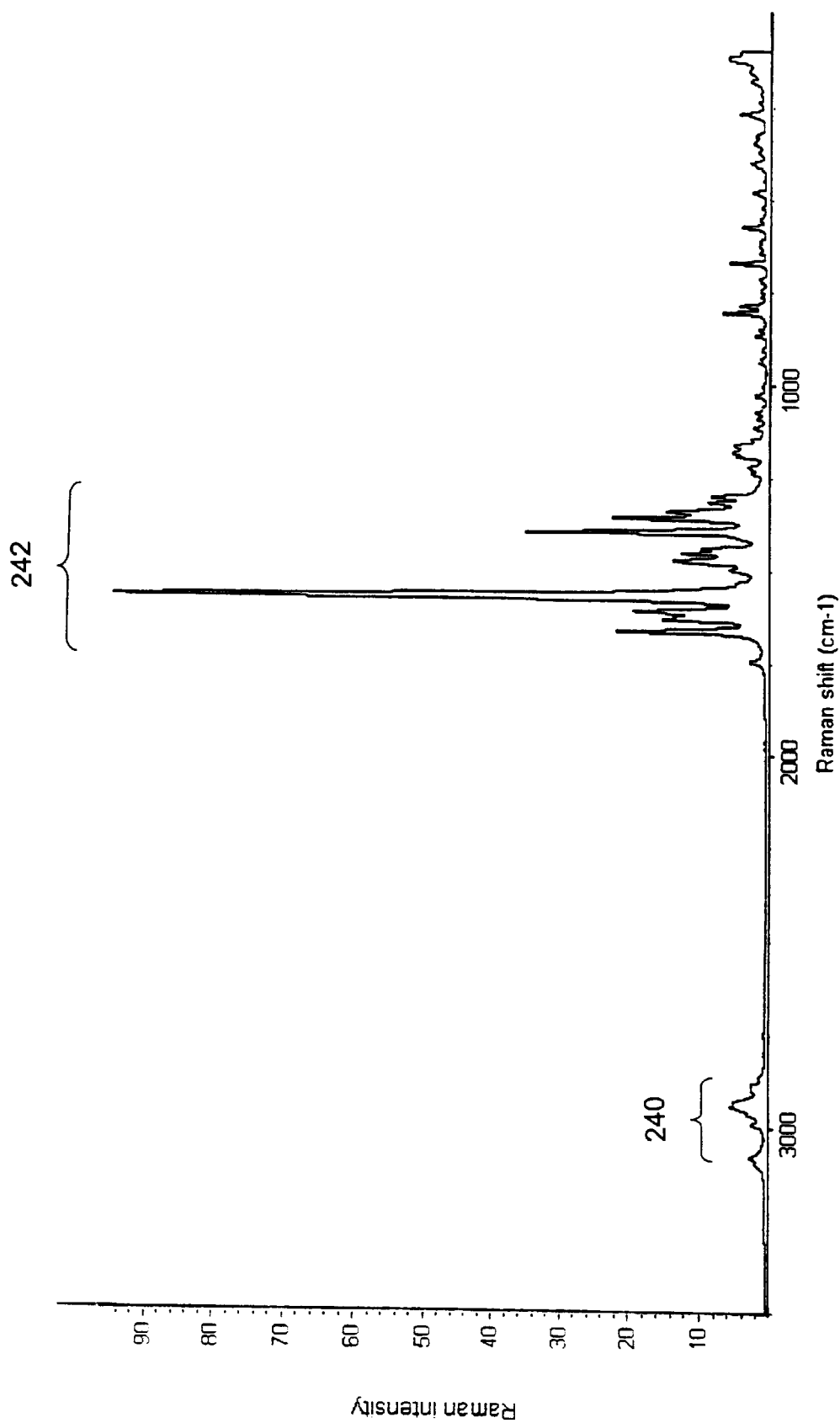
FIG. 24 is a plot of the Raman absorption spectrum for Form F.

The Raman spectrum for Form F is provided in FIG. 24. The Raman spectrum shows relatively weak aromatic and aliphatic CH stretches 240 between 3100 and 2800 cm$^{-1}$, and stronger bands 242 in the region from 1700–1300 cm$^{-1}$. The characterization data are consistent with the description of this form as a hydrate containing between one fourth and one third of an equivalent of water.

H. Form G polymorph of 9-nitrocamptothecin

Form B polymorph of 9-nitrocamptothecin may be made by crystallizing 9-nitrocamptothecin from reagent or HPLC grade dimethylformamide (reagent or HPLC grade DMF being substantially water free, defined as containing no more than a trace of water). For example, a saturated or near saturated solution of 9-nitrocamptothecin in DMF is prepared. The saturated or near saturated solution of 9-nitrocamptothecin in DMF is then crystallized from solution employing conventional methods for crystallizing organic compounds from organic solvents.

As it is well appreciated in the art of growing crystals in general that higher quality crystals, e.g. forming crystals having fewer lattice defects and proportionately less glassy material, are generally favored by conditions that favor slower crystal formation, including those slowing solvent evaporation and those affecting kinetics generally, the crystallization conditions may be appropriately be adjusted to obtain higher quality crystalline material as necessary. Thus, for example, if poor crystals are formed under an initial set of crystallization conditions, the solvent temperature may be reduced and ambient pressure above the solution may be increased relative to the initial set of crystallization conditions.

Figure 25:
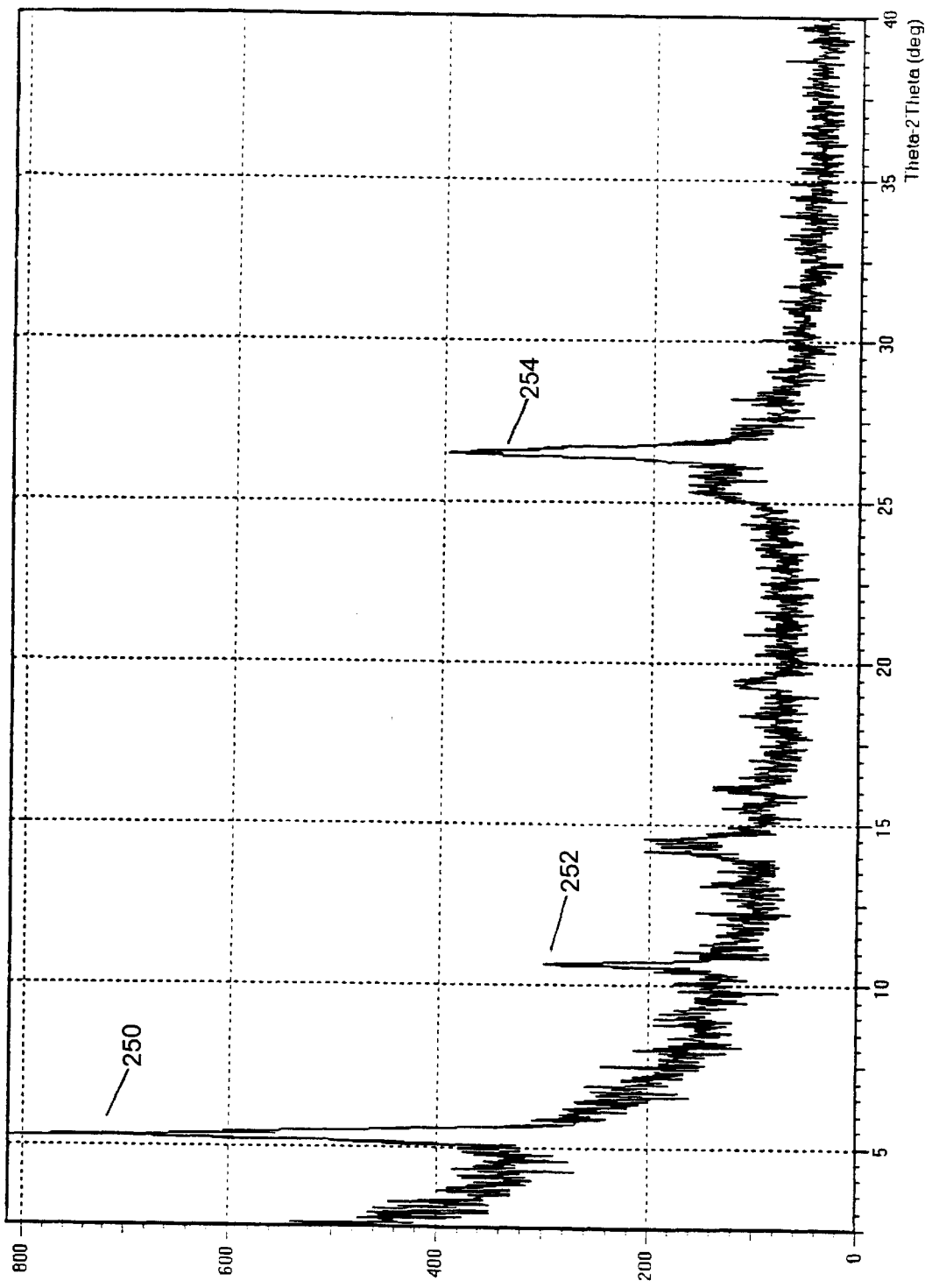
FIG. 25 is a plot of the XRPD pattern of Form G.

The XRPD pattern of Form G is provided in FIG. 25. It has major diffraction lines 250, 252 and 254 at about 5.4, 10.6 and 26.5 °2θ respectively. A few additional broad lines are observed as well. This pattern was obtained from DMF.

TGA data on Form G is summarized below in Table 14. It shows a rather gradual weight loss of 0.9% out to approximately 135° C., followed by a significant eight loss of 5.5% out to 235° C., with decomposition occurring above this temperature. The theoretical amount for a single equivalent of DMF solvent is approximately 15.7%.

TABLE 14

Thermal Data on Crystal Form G

| Form | DSC Results* | TGA Results** |
|------|--------------|---------------|
| G | endo 82.2, 150.2<br>exo 163.6, 273.0 | 6.4 |

*endo - endotherm, exo - exotherm, maximum temperature reported for transition
**percent weight change from 35 to 230° C.

Figure 26:
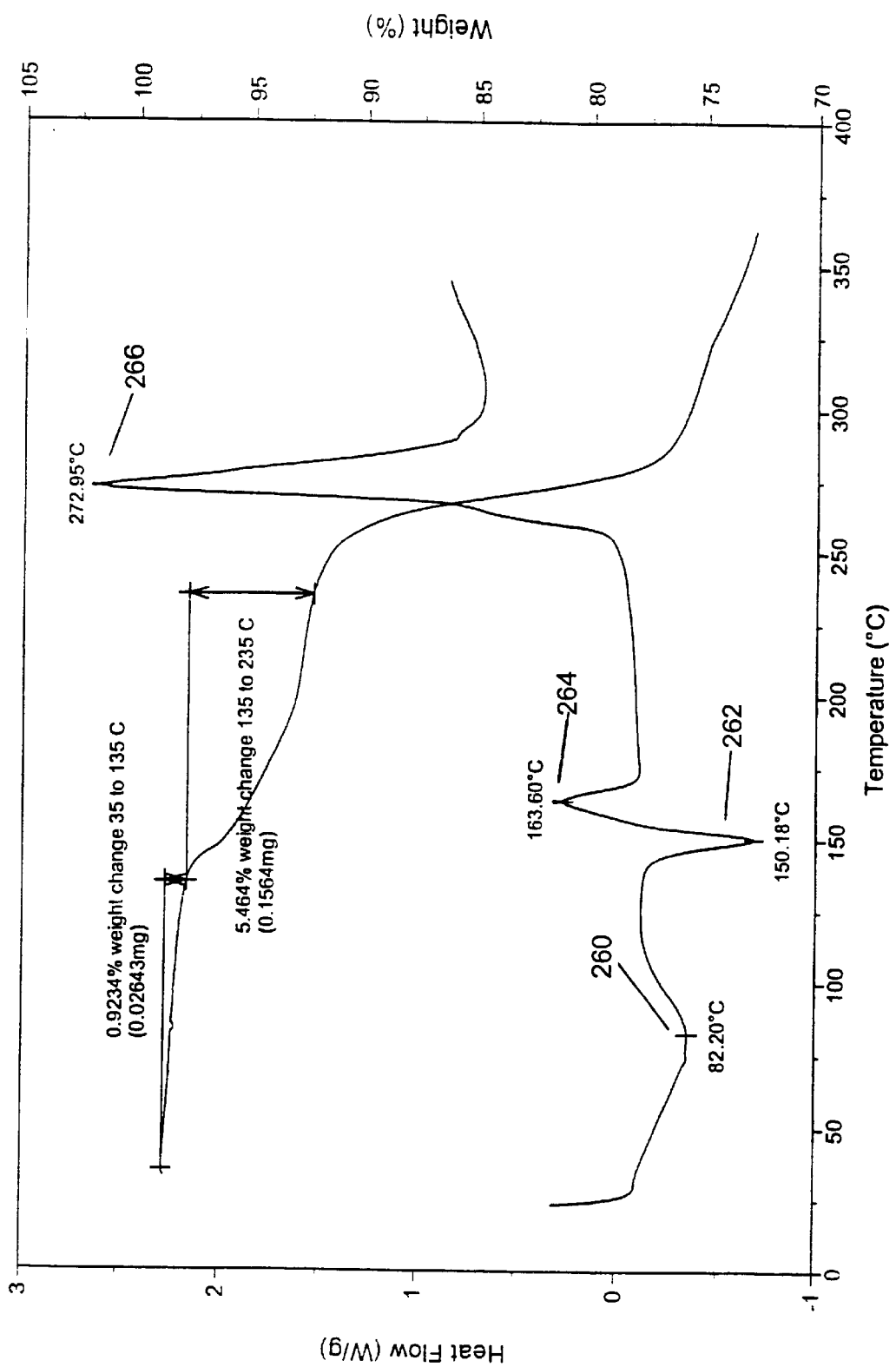
FIG. 26 is a plot of the TGA data and the DSC data for Form G.

The DSC curve for Form G is provided in FIG. 26. It is similar to the DSC curve for Form B and shows a broad endotherm 260 at 82.2° C. This broad endotherm may be assigned to loss of volatiles and is followed by a sharp endotherm 262 at about 150.2° C. and an exotherm 264 at 163.6° C., assigned to either a solvent loss or a melt followed by recrystallization. A melt endotherm is not observed prior to the decomposition exotherm 266 at about 273° C. This data is consistent with a mixed hydrate/solvate form.

Figure 27:
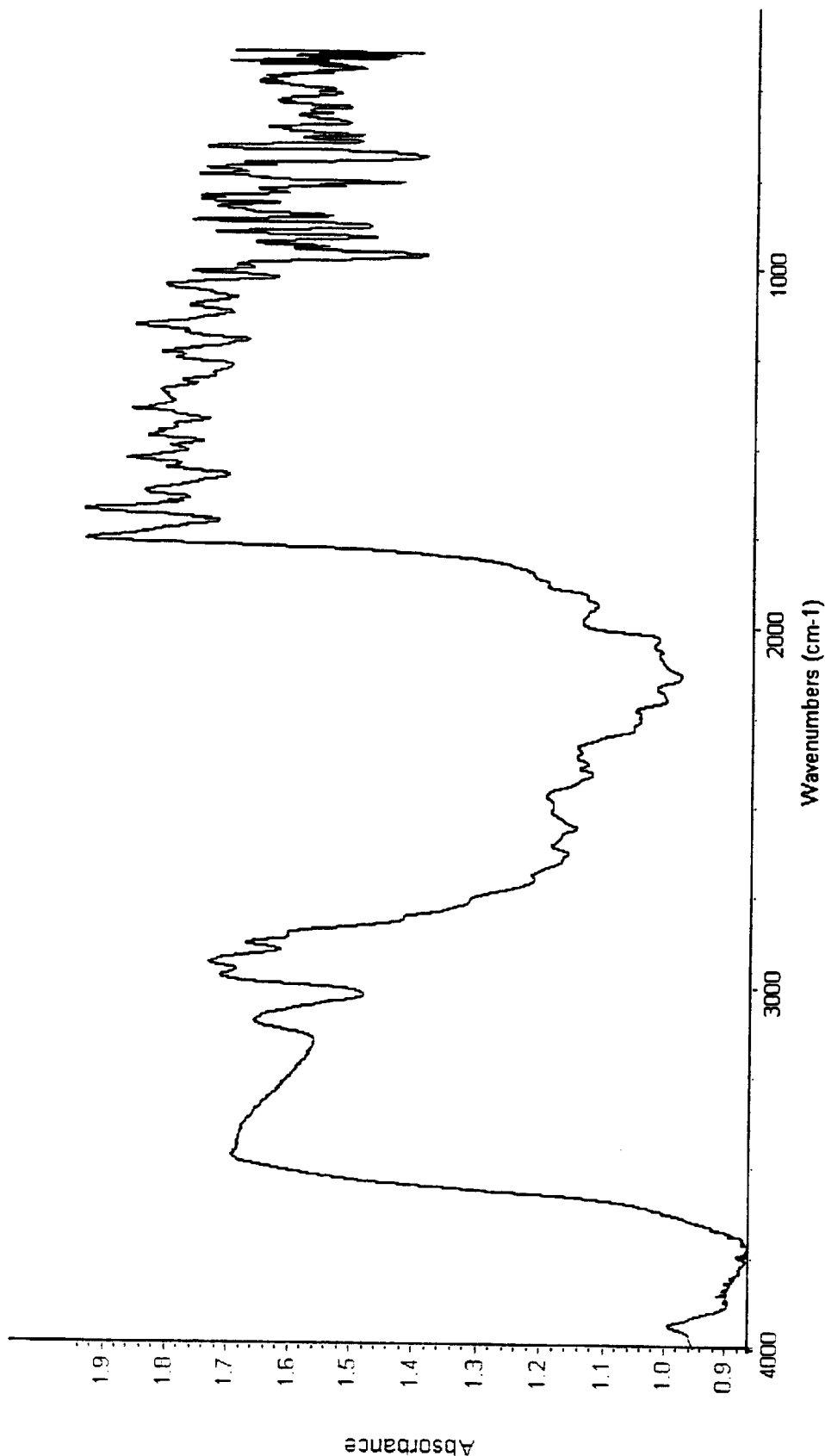
FIG. 27 is a plot of the IR absorption spectrum for Form G.
Figure 28:
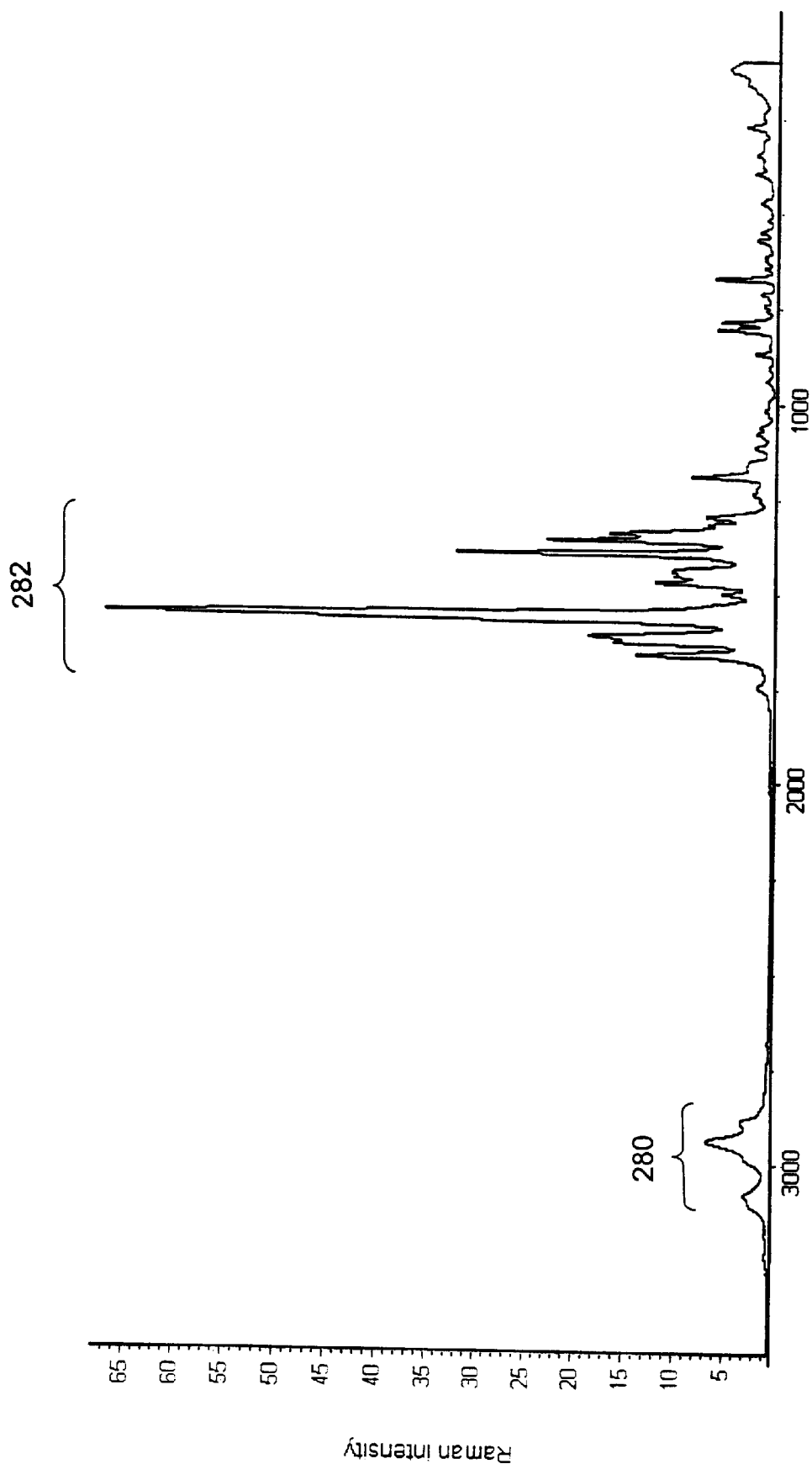
FIG. 28 is a plot of the Raman absorption spectrum for Form G.

The IR spectrum for Form G is plotted in FIG. 27 and the Raman spectrum is plotted in FIG. 28. The Raman spectrum shows relatively weak aromatic and aliphatic CH stretches 280 between 3100 and 2800 $cm^{-1}$, and stronger bands 282 in the region from 1700–1300 $cm^{-1}$. As characterized by the preceding data, Form G appears to be a relatively poorly crystalline mixed hydrate/solvate polymorph of 9-nitrocamptothecin.

I. Amorphous or Increased Amorphous Content Material

Figure 29:
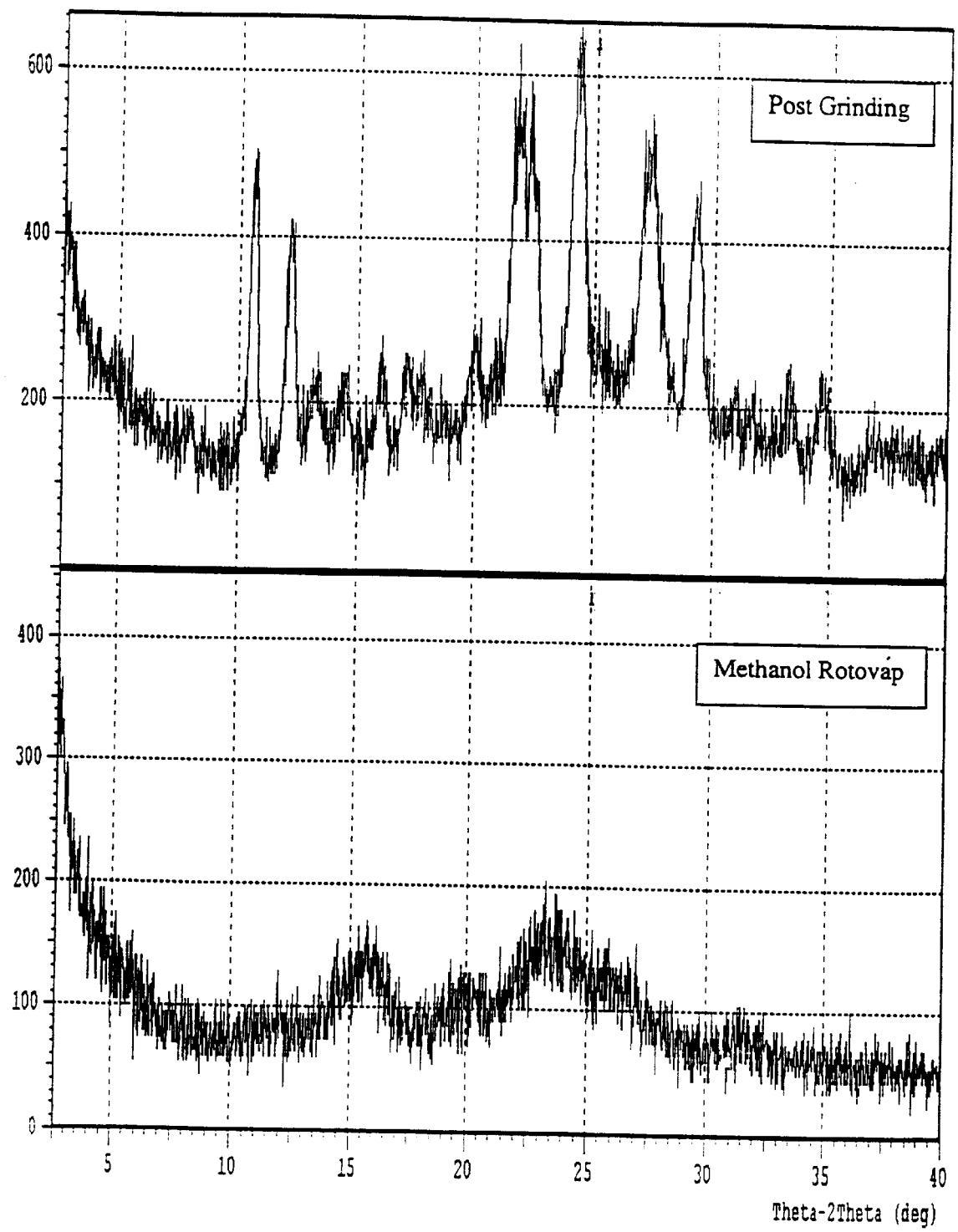
FIG. 29 is a plot of the XRPD pattern of ground 9-nitrocamptothecin Form A exhibiting broadened spectral lines indicative of the ground material having increased amorphous content compared to unground Form A.

The XRPD data for the increased amorphous content material obtained by grinding a crystalline polymorph are plotted in FIG. 29. This material is obtained from grinding Form A. Ground Form A has a discernable XRPD pattern, and is therefore crystalline as defined herein. Ground Form A exhibits a discernable broadening of the Form A XRPD pattern, indicative of increased amorphous content compared to Form A as crystallized from ethanol. Further grinding is expected to increase the amorphous content and further broaden the XRPD pattern with the limit of the XRPD pattern being so broadened that it cannot be discerned above noise. When the XRPD pattern is broadened to the limit of being indiscernable, the material is no longer a crystalline material having increased amorphous content relative to unground crystallized material, but is a material that is wholly amorphous as defined herein. Although the peaks that are present are consistent with form A material they are broadened considerably along with the appearance of an amorphous halo indicating that the material is losing crystallinity after grinding. No peaks were observed that would indicate grinding produces another form.

Amorphous material was also obtained after rapidly removing methanol by evaporation from a 9-nitrocamptothecin in methanol solution on a rotovap. The XRPD data for the amorphous material (wholly amorphous as defined herein, and denoted Form X) derived from rapid evaporation of 9-nitrocamptothecin dissolved in methanol is provided in FIG. 29.

2. Formulations and Administration Modalities

The present invention also encompasses pharmaceutical formulations comprising one or more 9-nitrocamptothecin polymorphs of the present invention and a pharmaceutical carrier or diluent, wherein the 9-nitrocamptothecin remains in its polymorphic form.

Formulations according to the present invention may be adapted for any type of administration where it is feasible to administer solid particles of a drug. For example, the formulatins can be administered orally, parenterally, intraperitoneally, intravenously, intraarterially, transdernally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally, optionally in a slow release dosage form. In particular embodiments, the 9-nitrocamptothecin polymorphs are administered orally, by inhalation or by injection subcutaneously, intramuscularly intravenously or directly into the cerebrospinal fluid.

A. Oral and Parenteral Formulations

According to one embodiment, one or more polymorphic forms may be formulated for oral administration. The concentration of the polymorphs given in any oral formulation is determined by the final desired formulation. The total amount of all polymorphs present in the formulation is preferably an amount that will allow a recommended dose to be conveniently administered. One factor in determining the amount of the polymorph or polymorphs contained in an oral dose is the required size of the delivery vehicle.

Solid dosage forms for oral administration include capsules, tablets, pills, powders, and granules. In solid dosage forms, the active agent is admixed with at least one inert pharmaceutically acceptable carrier such as sucrose, lactose, or starch. Such dosage forms can also comprise, as is normal practice, an additional substance other than an inert diluent, e.g., a lubricating agent such as magnesium stearate. With capsules, tablets, and pills, the dosage forms may also comprise a buffering agent. Tablets and pills can additionally be prepared with enteric coatings.

Liquid dosage forms for oral administration include pharmaceutically acceptable, suspensions and syrups, with the elixirs containing an inert diluent commonly used in the art, such as water. These compositions can also include one or more adjuvants, such as a surface stabilizing agent, a suspending agent, a sweetening agent, a flavoring agent or a perfuming agent. 9-nitrocamptothecin is maintained in any disclosed polymorph form when the invention is embodied as a liquid dosage form.

According to this aspect, the 9-nitrocamptothecin polymorph is mixed with other compounds or delivery devices to form stable compositions with enhanced therapeutic activity. These formulations permit oral administration to tumor-bearing subjects, such as human patients with cancer. For example, in one embodiment, the 9-ntirocamptothecin polymorph forms may be mixed with pharmaceautically acceptable powdered excipients, carriers and/or diluents. The compositions and amount of each additional material in the formulation will depend upon various factors, including, the speed of administration, the timing of drug delivery after administration of the formulation and final desired concentration. Examples of exicipents that may be included in such formulations include a pH adjustment compound, typically either a pharmaceutically acceptable acid or base, and/or a buffering agent, comprising approximately equimolar ratio of a weak acid or base and the conjugate salt thereof.

In one embodiment, the formulation may comprise a polymorph combined with a surface interaction inhibitor, which creates a physical barrier between adjacent particles. In this formulation, the 9-nitrocamptothecin is preferably a crystalline polymorph (e.g. a true solid) having a relatively small particle size, which is expected to stabilize the 9-nitrocamptothecin better than a glassy or amorphous, quasi-solid material having the same particle size. The small yet stable particles 9-nitrocamptothecin delivered in this composition are expected to have better bioavailability and higher therapeutic activity when administered orally compared to dosage forms having larger particle size, while having a longer shelf life than preparations comprising small glassy particles.

Preparations for parenteral administration include sterile aqueous or non-aqueous suspensions, and microsuspensions. Examples of non-aqueous vehicles are propylene glycol, polyethylene glycol, vegetable oils, such as olive oil and corn oil, gelatin, and injectable organic esters such as ethyl oleate. Those of skill in the art of formulating pharmaceutical preparations will appreciate that complete salvation of crystalline or amorphous solids is not encompassed by the instant invention and the polymorph should be insoluble in the carrier to preserve the polymorph that is to be employed in the specific formulation. Such dosage forms may also contain one or more adjuvants such as a preserving agent, for example a surface interaction inhibitor, a wetting agent and a dispersing agent. The dosage forms may be sterilized by, for example, filtration through a bacteria-retaining filter, by incorporating sterilizing agents into the compositions, by irradiating the compositions, or by heating the compositions. They can also be manufactured using sterile water, or some other sterile injectable medium, prior to use.

Pharmaceutical formulations for oral or parenteral administration may also comprise a 9-nitrocamptothecin polymorph-containing microsuspension, and may contain alternative pharmaceutically acceptable carriers, vehicles, additives, etc. particularly suited to oral or parenteral drug administration. Alternatively, a 9-nitrocamptothecin polymorph-containing microsuspension may be administered orally or parenterally without modification. Microsuspensions are thermodynamically stable dispersions of microcrystals, which may be stabilized by an interfacial film of surfactant molecules functioning as a dispersing agent (*Encyclopedia of Pharmaceutical Technology* (New York: Marcel Dekker, 1992), volume 9).

B. Pulmonary Administration

Any of the 9-nitrocamptothecin polymorphs may be employed for pulmonary administration. Both crystalline polymorphs, wherein the crystals are true solid materials, and wholly amorphous, glassy, quasi-solid polymorphs lend themselves to being rendered to an appropriate particle size for both dry and aerosolized liquid particle types of pulmonary delivery. The crystalline or glassy polymorphic forms of the 9-nitrocamptothecin is more stable over time than preparations wherein the 9-nitrocamptothecin molecules do not comprise a solid or quasi-solid, as when the 9-nitrocamptothecin molecules are solvated. By way of example rather than limitation, any crystalline polymorph 9-nitrocamptothecin can be used in a dry powder formulation for pulmonary delivery if it has been crystallized in microcrystalline form. Alternatively crystalline polymorphs of 9-nitrocamptothecin having may be ground or pulverized to obtain a sufficiently small particle size, which may render them a corresponding polymorph having increased amorphous content, or predominantly amorphous precipitate from rapid evaporation of solvent may be ground into a powdered glass form.

Dry powder formulations for pulmonary delivery include the crystalline or amorphous polymorph and any carrier suitable for pulmonary drug administration, although pharmaceutical sugars are generally preferred as carriers, e.g., fructose, galactose, glucose, lactitol, lactose, maltitol, maltose, mannitol, melezitose, myoinositol, palatinite, raffinose, stachyose, sucrose, trehalose, xylitol, and hydrates and combinations thereof. Selected components are initially combined and then blended to form a homogeneous, uniform powder mixture. Techniques for preparation of such powders are well known in the art; briefly, the preparation typically includes the steps of reducing the particle size of each component (as necessary), combining the individual components and blending. Techniques of reducing the particle size employ, by way of example, mills such as an air-jet mill or ball mill. Particle sizes having a diameter of between about 0.1 $\mu$m to about 65 $\mu$m are required for pulmonary administration. Blending methods include passing the combined powders through a sifter and blending the individual powders in a powder blender such as a "double cone" blender or a "V-blender." Regardless of the specific technique employed the resulting powder must be both homogeneous and uniform. Typically, the active agents will make up from about 0.10% to about 99% (w/w) of the total formulation.

Pulmonary formulations of the present invention may also be administered as aerosol compositions. Aerosol formulations are known to those skilled in the art and described, for example, in *Remington's Pharmaceutical Sciences*, 19$^{th}$ Ed. (Easton, Pa.: Mack Publishing Company, 1995). Briefly, the aerosol formulation of the invention is either a solution aerosol, in which the active agents are soluble in the carrier (e.g., propellant), or a dispersion aerosol, in which the active agents are suspended or dispersed throughout the carrier or carriers and optional solvent. In aerosol formulations, the carrier is typically a propellant, usually a liquefied gas or mixture of liquified gases. For example, the carrier may be a fluorinated hydrocarbon. Preferred fluorinated hydrocarbons are selected from trichloromonofluoromethane, dichlorodifluoromethane, dichlorotetrafluoroethane, chloropentafluoroethane, 1-chloro-1,1-difluoroethane, $1,1,1_{13}$ difluoroethane, octafluorocyclobutane, 1,1,1,2-tetrafluoroethane (HFA-134$a$), 1,1,1,2,3,3,3-heptafluoropropane (HFA-227) and combinations thereof. As is readily appreciated by one skilled in the art, the aerosol formulations of the invention may include one or more excipients. The aerosol formulations may, for example, contain: an antioxidant (e.g., ascorbic acid) for inhibiting oxidative degradation of the active agents; a dispersing agent (e.g., sorbitan trioleate, oleyl alcohol, oleic acid, lecithin, corn oil, and combinations thereof) for preventing agglomeration of particles; and/or a lubricant (e.g., isopropyl myristate) for providing slippage between particles and lubricating the components, e.g., the valve and spring, of the inhaler.

As described with respect to the dry powder formulations, the particle size released from aerosol formulations must be appropriate for pulmonary administration. Solution aerosols inherently produce small particles upon actuation of the inhaler because the active agent is expelled along with the carrier, i.e., propellant, solution as it evaporates. Consequently, solution aerosol administration produces sufficiently small particles, e.g., within a range of about 0.1 $\mu$m to about 65 $\mu$m, of active agents. The crystalline and amorphous polymorphs of 9-nitrocamptothecin of the invention may only be delivered via aerosol as a dispersion of solid in a liquid carrier.

Dispersion aerosols contain undissolved active agents in which particle size remains constant, i.e., the size of the particles in the dispersion aerosol remains unchanged during delivery of the active agent. The active agents must therefore have an appropriate particle size before formulation into a dispersion aerosol. Thus, techniques for reducing the particle size of active agents as described above for the dry powder formulations are equally applicable for preparing active agents having an appropriate particle size in a dispersion aerosol. Further, the same ranges of particle sizes preferred for the dry powder formulations are applicable to dispersion aerosols.

Aerosol formulations of the invention may be prepared by utilizing a cold filling process. First, the components of the aerosol formulation and an aerosol container are cooled to about −40° C., so that the carrier, i.e., propellant, is a liquid. All the components except for the carrier are then placed into the aerosol container. Next, the carrier is added and the components are mixed. A valve assembly is then inserted into place. Finally, the valve assembly is crimped so that the container is airtight. The assembled container bearing the inhalant formulation may be allowed to return to ambient temperature after assembly. As an alternative to the cold filling process, the aerosol formulation may be prepared by transfer of a carrier from a bulk container after all the components except for the carrier are placed into an aerosol container and a valve assembly is then inserted and crimped into place. The liquid carrier is then metered under pressure through the valve assembly from a bulk container or tank. After the carrier is metered in, the container is checked to ensure that the pressurized contents do not leak. For both of these methods of preparing aerosol formulations, the active agent will typically make up from about 0.1 wt. % to about 40 wt. % of the total formulation. Preferably the active agents make up about 1 wt. % to about 15 wt. % of the total formulation.

The pulmonary formulations of the present invention may also be a liquid composition for inhalation, as is well known in the art. See, e.g., *Remington: The Science and Practice of Pharmacy*, supra. For the 9-nitrocamptothecin polymorphs of the instant invention, the liquid composition must be a microsuspension. Such liquid formulations include one or more carriers in addition to the active agents. As mentioned above, care must be taken that a carrier does not solvate the polymorph is employed. An example of a carrier is a sodium chloride solution having concentration making the formulation isotonic relative to normal body fluid. In addition to the carrier, the liquid formulations may contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitan monopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Combining the components followed by conventional mixing effects a liquid formulation suitable for inhalation. Typically, the active agents will make up from about 0.01% to about 40% of the total formulation.

Various known devices may be used to administer pulmonary formulations, whether dry powder, aerosol or liquid. Dry powder inhalers are well known to those skilled in the art and are used to administer the aforementioned dry powder formulations. Suitable dry powder inhalation devices for administering the present formulations include, for example, TURBOHALER® (Astra Pharmaceutical Products, Inc., Westborough, Mass.), ROTAHALER® (Allen & Hanburys, Ltd., London, England). Aerosol formulations may be administered via pressurized metered-dose inhalers. Liquid formulations of the invention may be administered via a pump spray bottle or nebulizer.

Other active agents may also be included in the formulations of the invention, including other anti-proliferative, anti-neoplastic or anti-inflammatory or bronchodilating agents that dilate the airway and effect deeper delivery, especially for pathologies involving inflammation of the bronchi or alveoli, or airway obstruction, for example lung and broncoalveolar carcinomas. Agents that perform both these functions, such as long acting β adrenergic agonists, including salmeterol xinafoate, and phosphodiesterase inhibitors, including theophylline and other hypoxanthines, have been shown to exert a synergistic anti-inflammatory effect in inflammatory pathophysiologic processes in the lung by Pang et al. (2000) *Am. J. Respir. Cell Mol. Biol.* 23(1):79–85.

Examples of suitable additional active agents to be coadministered with 9-nitrocamptothecin in the treatment of proliferative respiratory disorders involving inflammation and/or obstruction include, without limitation, bronchodilators, including β adrenergic agonists, anticholinergics, phosphodiesterase inhibitors suitable for inhalation, and corticosteroids. Combinations of bronchodilators may also be used. Long acting β adrenergic agonists are particularly preferred, as they will not only provide anti-inflammatory effects that often important in treating neoplastic pathologies of the respiratory system, but may also effect deeper delivery into the lung; this is especially important for lung and bronchoalveolar carcinomas involving alveolar inflammation. Likewise, any glucocorticoid therapeutically suitable for administration by inhalant or a pharmaceutically suitable salt ester or other derivative thereof may be included for co-administration by inhalant.

As alluded to above, bronchodilators are useful to ensure delivery of active agent deep into the lungs. Typical bronchodilators of the anticholinergic type include, by way of example rather than limitation, atropinic compounds such as isatropium, which have been shown to be strongly synergistic (Dusser (1998) *Ann. Fr. Anesth. Reanim.* 17(Suppl. 2):40s–42s) with β agonists, specifically $β_2$ agonists, in bronchodilation for acute asthma and are expected to exert similar effects when used to open the airways to ensure deep delivery to the alveoli for delivery of anti-inflammatory agent. Typical bronchodilators of the β adrenergic agonist class include, but are not limited to, albuterol, bitolterol, clenbuterol, fenoterol, formoterol, levalbuterol (i.e., homo-chiral (R)-albuterol), metaproterenol, pirbuterol, procaterol, reproterol, rimiterol, salmeterol and terbutaline. The bronchodilator may be present in the formulation as a salt, ester, amide, prodrug, or other derivative, or may be functionalized in various ways as will be appreciated by those skilled in the art.

Other anti-inflammatory drugs can be combined with 9-nitrocamptothecin. Corticosteroids and non-steroidal anti-inflammatory drugs (NSAIDS) are potential combinatorial therapy agents, and already used in the treatment of inflammatory airway disease and neoplasms in general. Cromolyn sulfate and the new class of leukotriene inhibitors are also used in treating inflammatory disease, and may therefore be employed inconjunction with the 9-nitrocamptothecin crystalline and amorphous polymorphs for inhalation therapy of both neoplasms associated with inflammation and primary inflammatory proliferative lung pathologies. Agents that are not primarily anti-inflammatory which have been evidenced to have anti-inflammatory activity include the long acting agonists and theophylline, as noted above, and macrolide antibiotics (Cazzola et al. (2000) *Monaldi Arch. Chest Dis.* 55(3):231–6), which include erythromycin and its derivatives, e.g., azithromycin and clarithromycin.

Co-administration of antibiotics, including those with anti-inflammatory activity, or anti-viral agents, with the crystalline and amorphous polymorphs of the instant invention is desirable for treatment of pulmonary neoplasias, which predispose the lungs to infection, and for treating, proliferative inflammatory diseases of infectious etiology, such as pulmonary tuberculosis and viral pneumonitis.

C. Transdermal Administration

Particulate suspensions, microsuspensions and nano suspensions as well as emulsifications of various particulate sizes, including the particulate sizes appropriate for pulmonary administration may be converted to transdermal delivery of 9-nitrocamptothecin. Alternatively larger size crystalline and/or amorphous polymorphs of the invention may be formulated as an emulsified, including microemulsified, dispersion, with addition of an appropriate emulsifying agent. However the particulate sizes obtained for pulmonary administration may be directly combined with an appropriate agent that preserves the particles while permitting the diffusion of 9-nitrocamptothecin molecules therethrough and transdermally upon application through the skin 3. Indications The 9-nitrocamptothecin polymorphs may be used to treat any disease state in which 9-nitrocamptothecin is therapeutically effective. In order to take advantage of the novel polymorphs of the present invention, the pharmaceutical formulations in which the polymorphs are incorporated and administered should retain their polymorphic form.

According to one embodiment, a method is provided for treating a disease state comprising administering to a patient a formulation comprising one or more 9-nitrocamptothecin polymorphs.

In one variation, a formulation comprising the 9-nitrocamptothecin polymorph is administered to a patient having a disease state associated with an undesirable or uncontrolled cell proliferation. Such indications include, for example, restenosis (e.g. coronary, carotid, and cerebral lesions), benign tumors, various types of cancers such as primary tumors and tumor metastases, abnormal stimulation of endothelial cells (atherosclerosis), insults to body tissue due to surgery or other events leading to formation of scar tissue, abnormal wound healing, abnormal angiogenesis, diseases that produce fibrosis of tissue, repetitive motion disorders, disorders of tissues that are not highly vascularized, proliferative responses associated with organ transplants and various inflammatory proliferative diseases.

Generally, cells in a benign tumor retain their differentiated features and do not divide in a completely uncontrolled manner. A benign tumor is usually localized and nonmetastatic. Specific types of benign tumors that can be treated using the present invention include, without limitation, hemangiomas such as cavernous hemangioma, hepatocellular adenoma, cavernous hemangioma, focal nodular hyperplasia, acoustic neuromas, neurofibroma, bile duct adenoma, bile duct cystanoma, fibroma, lipomas, benign bone tumors, leiomyomas, mesotheliomas, teratomas, myxomas, nodular regenerative hyperplasia, trachomas and granulomatous inflammatory diseases both infectious, such as pyogenic granulomas, and non-infectious or idiopathic, such as sarcoidosis and berylliosis.

In a neoplasia such as a malignant tumor, cells become undifferentiated, do not respond to physiologic cell proliferation control signals, and multiply in an uncontrolled manner. The malignant tumor is invasive and capable of spreading to distant sites (metastasizing). Malignant tumors and other neoplasias may usually be divided into primary and secondary neoplasias. A primary neoplasia arises directly from the tissue of origin and may spread to contiguous tissues and organs by local invasion. A secondary neoplasia, or metastasis, is exemplified by a tumor that originated elsewhere in the body but has now spread to a distant organ. The common routes for spread of neoplasia are direct growth into adjacent structures, and metastatic spread through the vascular or lymphatic systems, and tracking along tissue planes and body spaces including peritoneal fluid, cerebrospinal fluid, etc.

Specific types of cancers or neoplasias, both primary and secondary, that can be treated using this invention include both carcinomas and sarcomas. Examples of specific carcinomas and sarcomas include leukemia, breast cancer, skin cancer, bone cancer, prostate cancer, liver cancer, lung cancer, neurological tumors of the brain, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteosarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyomas, cervical dysplasia and other in situ carcinomas, neuroblastoma, retinoblastoma, soft tissue sarcoma, malignant carcinoid, topical skin lesion, mycosis fungoides, rhabdomyosarcoma, Kaposi's sarcoma, osteogenic and other sarcomas, malignant hypercalcemia, renal cell tumor, polycythemia vera, adenocarcinomas, glioblastoma multiforma, leukemias, lymphomas, melanoma, epidermoid carcinomas.

Treatment of abnormal cell proliferation due to insults to body tissue during surgery may be possible for a variety of surgical procedures, including joint surgery, bowel surgery, and keloid scarring. Diseases that produce fibrotic tissue include emphysema. Repetitive motion disorders that may be treated using the present invention include carpal tunnel syndrome.

The proliferative responses associated with organ transplantation that may be treated using this invention include those proliferative responses contributing to potential organ rejections or associated complications. Specifically, these proliferative responses may occur during transplantation of the heart, lung, liver, kidney, and any foreign or non-self cells, tissues, organs or organ systems.

Abnormal angiogenesis that may be may be treated using this invention include those abnormal angiogenesis accompanying rheumatoid arthritis, ischemic-reperfusion related brain edema and injury, adrenal cortical ischemia, ovarian hyperplasia and hypervascularity, polycystic ovary syndrome, endometriosis, psoriasis, diabetic retinopaphy, and other ocular angiogenic diseases such as retinopathy of prematurity (retrolental fibroplastic disease), macular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

In another embodiment of the present invention, a method is provided for treating diseases associated with undesired and uncontrolled angiogenesis. The method comprises administering to a patient suffering from uncontrolled angiogenesis a therapeutically effective amount of 9-nitrocamptothecin, such that formation of blood vessels is inhibited. The particular dosage of 9-nitrocamptothecin required to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the composition of the present invention may be used to treat a variety of diseases associated with uncontrolled angiogenesis such as retinal/choroidal neovascularization and corneal neovascularization. Examples of retinal/choroidal neovascularization include, without limitation, Best's disease, myopia, optic pits, Stargart's disease, Paget's disease, vein occlusion, artery occlusion, sickle cell anemia, sarcoid, syphilis, pseudoxanthoma elasticum carotid abostructive diseases, chronic uveitis/vitritis, mycobacterial infections, Lyme disease, systemic lupus erythematosis, retinopathy of prematurity, Eale's disease, diabetic retinopathy, macular degeneration, Behcet's disease, infections causing a retinitis or choroiditis, ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, Sjogren's syndrome, acne rosacea, phylectenulosis, diabetic retinopathy, retinopathy of prematurity, corneal graft rejection, Mooren ulcer, Terrien's marginal degeneration, marginal keratolysis, polyarteritis, Wegener granulomatosis, sarcoidosis, scleritis, pemphigoid, radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In yet another embodiment of the present invention, a method is provided for treating chronic inflammatory diseases associated with uncontrolled angiogenesis. The method comprises administering to a patient suffering from a chronic inflammatory disease associated with uncontrolled angiogenesis a therapeutically effective amount of the composition of the present invention, such that formation of blood vessels is inhibited. The chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using the composition of the present invention alone or in conjunction with other anti-inflammatory agents may prevent the formation of the granulomas, thereby alleviating the disease. Examples of chronic inflammatory disease include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and ascending colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

These inflammatory bowel diseases are generally caused by chronic granulomatous inflammatory pathophysiologic processes. Inflammatory bowel disease may affect the entire gastrointestinal tract, typically involving new capillary sprouts surrounded by a cylinder of inflammatory cells. Inhibition of angiogenesis by the composition of the present invention should inhibit the formation of the sprouts and prevent the formation of granulomas. The inflammatory bowel diseases also exhibit extra intestinal manifestations, such as skin lesions. Such lesions are characterized by inflammation and angiogenesis and can occur at many sites other the gastrointestinal tract. Inhibition of angiogenesis by the composition of the present invention should reduce the influx of inflammatory cells and prevent, halt or slow pathogenesis of the lesion.

Sarcoidois, another chronic inflammatory disease, is characterized as an idiopathic multisystem granulomatous disorder. Berylliosis resembles sarcoidosis histopathologically, but is known to be caused by the element Beryllium. The granulomas of sarcoidosis and berylliosis histopathologically resemble the non-caseating granulomas of *Mycobacterium tuberculosis* and other diseases caused by Mycobacteria, but caseating granulomas found in *M. Tuberculosis* infection are absent in both berylliosis and sarcoidosis. The granulomas of this disease can form anywhere in the body and, thus, the symptoms depend on the site of the granulomas and whether the disease is active. The formation of sarcoid granulomas is facilitated by the angiogenic capillary sprouts, which provide a constant supply of inflammatory cells. By using the composition of the present invention to inhibit angiogenesis, such granuloma formation can be inhibited.

Psoriasis, also a chronic and recurrent inflammatory disease, is characterized by papules and plaques of various sizes. Treatment using the composition of the present invention alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using the composition of the present invention alone or in conjunction with other anti-RA agents should prevent the formation of new blood vessels necessary to maintain the chronic inflammation and provide the RA patient relief from the symptoms.

The composition of the present invention may also be used in conjunction with other anti-angiogenesis agents to inhibit undesirable and uncontrolled angiogenesis.

Examples of anti-angiogenesis agents include, but are not limited to, retinoic acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d-1,3,4-dehydroproline, thiaproline], α, α-dipyridyl, β-aminopropionitrile fumarate, 4-propyl-5-(4-pyridinyl)-2 (3h)-oxazolone; methotrexate, mitoxantrone, heparin, interferons, 2 macroglobulin-serum, chimp-3, chymostatin, β-cyclodextrin tetradecasulfate, eponemycin, fumagillin, gold sodium thiomalate, d-penicillamine (CDPT), β-1-anticollagenase-serum, α-2-antiplasmin, bisantrene, lobenzarit disodium, n-(2-carboxyphenyl-4-chloroanthronilic acid disodium or "CCA", thalidomide; angiostatic steroid, carboxyaminoimidazole; metalloproteinase (metalloprotease) inhibitors such as BB94. Other anti-angiogenesis agents include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) *Nature Medicine* 5 5:1359–64.

In all embodiments, the term "effective amount" is understood as a medical art term, that is, the dose schedule and route of administration of the drug that gives the best therapeutic value and convenience to the patient.

EXAMPLES

The following examples set forth methods for analyzing the compositions of the present invention, studies regarding the characterization of their physical and chemical properties and methods of preparing the formulations according to the present invention.

1. Preparation of Samples

Three samples of 9-nitrocamptothecin were received from SuperGen Pharmaceutical Research Institute. A representative XRPD pattern exhibited by these samples is provided in FIG. 1. The polymorphic form giving this pattern is designated Form A.

2. Characterizing Stability in a Solvent by Interconversion of Forms

The initial material characterized was designated Form A and was isolated by direct crystallization of 9-nitrocamptothecin from an acetone/ethanol solvent mixture. Form B was obtained from either acetone or dichloromethane and appears to be a hemihydrate. Form C appears to be a mono tetrahydrofuran (THF) solvate. Form D, which was obtained by crystallization from an acetonitrile based solvent, appears to be an acetonitrile mono-solvate. Form E was which was obtained by crystallization from a chloroform based solvent, appears to be a ¼ equivalent chloroformic solvate. Form F has been obtained by interconversion from certain polymorphs, notably Forms B, C and D, typically in a dimethylformamide and water (75%/25%, v/v), see supra. Form F has also been obtained by crystallization from acetone/H$_2$O (80%/20%, v/v). Form G was obtained by direct crystallization of 9-nitrocamptothecin from dimethylformamide and appears to be a solvate/hydrate.

A. Characterizing Solubility

A weighed sample of 9-nitrocamptothecin (typically 10 to 20 mg) was treated with aliquots of the test solvent. Solvents were either reagent or HPLC grade. The aliquots were typically either 150 μL or 1 mL. Between additions the mixture was typically shaken or sonicated. Whether the solids dissolved was judged by visual inspection, an approximate solubility was obtained. These approximate solubilities are provided below in Table 15.

The solution was filtered followed by one of several different final processing steps, which are reported below as conditions in Table 16.

TABLE 15

Approximate Solubilities of 9-nitrocamptothecin

| Solvent[a, b] | Solubility (mg/mL)[c] | Notebook No. |
| --- | --- | --- |
| Acetone | <1 | 294-63-01 |
| acetonitrile (ACN) | <2 | 294-63-07 |
| Dichloromethane | 2 | 294-61-02 |
| dimethylformamide (DMF) | 8 | 294-65-02 |
| Ethanol | <3 | 294-63-02 |
| Ethylacetate | <3 | 294-63-04 |
| Hexanes | <2 | 294-65-03 |
| Methanol | <2 | 294-61-03 |
| methyl ethyl ketone (MEK) | <3 | 294-64-02 |
| tetrahydrofuran (THF) | <2 | 294-63-06 |
| Toluene | <2 | 294-64-01 |
| Water | <4 | 294-63-03 |

[a]The procedure was to add the test solvent in measured portions (usually 150 μL each) to an accurately-weighed sample of 9-nitrocamptothecin (usually about 15 mg) with shaking, stirring, or sonication at ambient temperature until a clear solution resulted. If a clear solution was not obtained, the values for solubilities are listed as "less than".
[b]Solvents are listed in alphabetical order.
[c]Solubilities were calculated based on the total solvent used to give a solution and rounded to the nearest whole number; actual solubilities may be greater due to the volume of the solvent portions utilized or to slow rates of dissolution.

TABLE 16

Polymorph Screen of 9-nitrocarnptothecin

| Sample Source | Conditions[a] | Habit[b] |
| --- | --- | --- |
| Lot no. 99-064 (SSCI no. 8499) | as received | — |
| Lot no. 99-064 (SSCI no. 8500) | as received | — |
| Lot no. 99-064 (SSCI no. 8501) | as received | — |
| Lot no. 99-064 | 10' grind | Nd |
| Lot no. 99-064 | melt | black solids |
| Acetone | FE | Needles |
|  | SE | Needles |
|  | SC (45° C.) | Needles |
|  | SC (45° C.) | Needles |
|  | SC (45° C.) | Needles |
|  | SC (45° C.) | Needles |
|  | SC (45° C.) | Needles |
|  | SC (45° C.) | Needles |
|  | SC (45° C.) | Nd |
|  | SC(45° C.) | Nd |
| acetone/ethanol (1:1) | SL, RT, 3 hrs | Nd |
|  | SL, 40° C., 3 hrs | Nd |
|  | SL, reflux, 3 hrs | Nd |
| Acetonitrile (ACN) | FE | Unknown |
|  | SH | Rods |
|  | SH | needles/rods |
|  | SH | needles/rods |
|  | SH | needles/rods |
|  | SH | Nd |
|  | SH | Nd |
|  | SC (60° C.) | plates, rods |

TABLE 16-continued

Polymorph Screen of 9-nitrocarnptothecin

| Sample Source | Conditions[a] | Habit[b] |
|---|---|---|
| Chloroform | FE | Needles |
|  | FE | Needles |
|  | FE | Needles |
|  | FE | Needles |
|  | SE | Needles |
|  | SE | Nd |
|  | SE | Nd |
|  | SC (45° C.) | Needles |
| Dichloromethane (DCM) | FE | Needles |
|  | FE | Nd |
|  | SE | Needles |
|  | SC (45° C.) | Needles |
|  | SC (45° C.) | Needles |
|  | SC (45° C.) | Needles |
|  | RV (50° C.) | Unknown |
|  | RV (50° C.) | Nd |
| Dimethylformamide | FE | Unknown |
|  | SE | Needles |
|  | SC (60° C.) | Unknown |
| Ethanol | FE | Unknown |
|  | SH | needles, rods |
|  | SC (60° C.) | Needles |
| Ethylacetate (EtOAc) | FE | Needles |
|  | SH | Rods |
|  | SC (60° C.) | Needles |
| Heptane | FE | no solids |
|  | SC (60° C.) | Nd |
| Hexanes | FE | no solids |
|  | SH | needles, rods |
|  | SC (60° C.) | Unknown |
| Methanol | FE | Unknown |
|  | SH | needles, rods |
|  | SC (60° C.) | Needles |
|  | RV (50° C.) | Unknown |
|  | RV (50° C.) | Unknown |
|  | RV (50° C.) | Unknown |
| Methylethylketone (MEK) | FE | Needles |
|  | SH | Rods |
|  | SC (60° C.) | Needles |
| Tetrahydrofuran (THF) | FE | Unknown |
|  | FE | Unknown |
|  | FE | Unknown |
|  | FE | Unknown |
|  | FE | Nd |
|  | SE | Nd |
|  | SC (60° C.) | Unknown |
| Toluene | FE | Needles |
|  | SH | needles, rods |
|  | SC (60° C.) | Needles |
| Water (H$_2$O) | FE | Unknown |
|  | SH | needles, rods |
|  | SC (60° C.) | unknown paste |

[a]FE = fast evaporation; SE = slow evaporation, SC = slow cool, SH = shaker, SL = slurry, RV = roto-vap
[b]nd = morphology not determined
[c]am = amorphous sample, ins = insufficient sample, lxt = low crystallinity, PO = preferred orientation, pks = extra peaks observed Fast evaporation (FE) indicates the filtered solution was left in an open vial under ambient conditions. Slow evaporation (SE) indicates the resulting solution was left under ambient conditions in a vial covered with aluminum foil containing pinholes. In some cases, the solvent was removed using a rotary evaporator (RV) with the sample bath temperature at 50° C.

The same procedure was repeated at elevated temperature (45 or 60° C.) by keeping the mixture on a hot plate at the desired temperature. The resulting solution was rapidly filtered into a vial kept on the same hot plate. The heat source was turned off and the hot plate and vial were allowed to cool to ambient temperature. The vial was then allowed to stand at ambient temperature overnight. The presence or absence of solids was noted. If sufficient solids were present, the solution was filtered and the solids collected. If insufficient solids were present, the vial was placed in a refrigerator overnight. Again the presence or absence of solids was noted and, if there were none, the vial was placed in a freezer overnight. Solids were removed by filtration and allowed to dry in the air.

Solubilities were estimated from these experiments based on the total solvent used to give a solution. Duplicate runs were averaged. The actual solubilities may be greater than those calculated due to the size of the solvent aliquots used, or due to a slow rate of dissolution. If dissolution did not occur during the experiment the solubility is expressed as "less than."

9-nitrocamptothecin slurries were agitated for 3 to 4 days in a shaker block at ambient temperature (slurry). Solids were removed by filtration and allowed to dry in the air. The remaining clear, yellow solutions were left for fast evaporation.

Crystallizations by addition of anti-solvent were performed by filtering a saturated solution of 9-nitrocamptothecin in DMF dropwise into 5 ml of an antisolvent. The antisolvents employed for the crystallization experiments included acetone, ethyl acetate, methyl ethyl ketone, toluene, and water. If solid precipitate was not present after the dopwise addition through a filter, the solution was capped and refrigerated. The sample was monitored periodically after beginning refrigeration, and if precipitate appeared, it was removed by filtration and allowed to air dry.

Hygroscopicity was investigated by placing a sample in a sealed chamber at room temperature and 95% relative humidity for 20 days. Weight gain/loss or TGA were not measured in the course of this study of hygroscopicity. An XRPD pattern was obtained on the solid remaining after 20 days and compared to the starting material.

Dehydration/desolvation studies were conducted by placing a sample under continuous vacuum at room temperature for 14 days. An XRPD pattern was obtained on the remaining solid and compared to the starting material.

A solidified melt of 9-nitrocamptothecin was produced by slowly heating the sample on a hot bench until a visual melt was observed and then quickly cooling the sample to ambient temperature. As the material began to melt, it turned dark and bubbled. The resulting dark material was not analyzed further due to decomposition.

9-nitrocamptothecin as received, e.g. Form A, was ground in an amalgamator for 10 minutes. The sample was then analyzed using XRPD. The observed XRPD pattern of the ground Form A was that of Form A with noticeable line broadening indicative of an increased proportion of glassy material relative to the unground Form A.

B. Characterizing Solubility and Interconversion of Forms

Interconversion experiments were carried out using Forms A, B, C, D, and E in two solvent systems, toluene and dimethylformamide/water (75%/25%, v/v). The experimental data indicate that in toluene, Form A is the most stable polymorph and Form B is more stable than Form C or Form E. In the DMF/H2O solvent mixture, Form F appears to be the most stable hydrated form, but form A was also isolated from this solvent mixture.

These interconversion experiments were carried out by making slurries containing two or more forms in saturated toluene or DMF/water (75/25) solutions. The slurries were agitated for 7 days at ambient temperature either in a shaker block or on a rotating wheel. The insoluble solids present after the agitation were recovered by filtration and analyzed using XRPD.

3. Characterization

A. X-Ray Powder Diffraction

X-ray powder diffraction analyses were carried out on a Shimadzu XRD-6000 X-ray powder diffractometer using Cu Kα radiation having a wavelength of 1.5406 Å. The instrument is equipped with a fine-focus X-ray tube. The tube power was set by setting potential difference at 40 kV, and current 40 mA. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40°2θ was performed. A silicon standard was analyzed each day to check the instrument alignment. Each sample was analyzed in a quartz sample holder. A variable temperature (VT-XRPD) experiment was performed on one form. The sample was prepared for analysis by pressing it into a variable temperature holder. A powder pattern was collected initially at 35° C. and again, after heating, at 200° C.

B. Thermo and Thermogravimetric Analysis

Thermogravimetric analysis (TGA) was carried out on a TA Instruments TGA 2050. The calibration standards were nickel and alumel. Approximately 2–7 mg of sample was placed on a clean, platinum pan, accurately weighed, and inserted into the TGA furnace. The samples were heated in nitrogen at a rate of 10° C./min, from 35° C. to a final temperature of 375° C.

DSC data were obtained on a TA Instruments DSC 2920. The calibration standard was indium. Approximately 1.5–2.5 mg of sample was placed into a DSC pan, and the weight accurately recorded. The pans were hermetically sealed with a pinhole to allow for pressure release. Note that the observed volatilization temperatures may be higher than those obtained in open pans due to pressure effects. The samples were heated under nitrogen at a rate of 10° C. min, from 25° C. to a final temperature of 350° C.

Hot-stage microscopy was carried out using a Wagner & Munz apparatus consisting of a Kofler stage mounted on a Leica Microscope. The stage temperature was calibrated using vanillin and caffeine USP standards each day prior to running samples. For each sample, a small quantity was placed on a microscope slide and covered. Samples were heated at approximately 4° C./min. and images were captured periodically using a 10x objective lens and a CCD camera. A cross-polarizing filter was used to observe birefringence.

C. Infrared Spectroscopy

Mid-IR spectra were acquired on a Nicolet model 860 Fourier transform IR spectrophotometer equipped with a globar source, Ge/KBr beamsplitter, and deuterated triglycine sulfate (DTGS) detector. A Spectra-Tech, Inc. diffuse reflectance accessory was utilized for sampling. Each spectrum represents 128 co-added scans at a spectral resolution of 2 $cm^{-1}$, except for sample 270–86–01, for which the spectrum was obtained with 256 scans at a resolution of 4 $cm^{-1}$. A background data set was acquired with an alignment mirror in place. A single beam sample data set was then acquired. Subsequently, a Log 1/R (R=reflectance) spectrum was acquired by taking the ratio of the two data sets against each other. The spectrophotometer wavelength was calibrated with polystyrene at the time of use.

D. Raman Spectroscopy

Raman spectra were acquired on a Raman accessory interfaced to a Nicolet Magna 860 Fourier transform infrared spectrometer utilizing an excitation wavelength of 1064 nm and approximately 0.5 W of Nd:YAG laser power. A routine spectrum represents 128 co-added scans at a spectral resolution of 4 $cm^{-1}$. Each sample was prepared for analysis by placing it in a 5-mm diameter glass tube and positioning this tube in the spectrometer. The spectrometer was calibrated (wavelength) with sulfur and cyclohexane at the time of use.

E. NMR Spectroscopy

Solution state $^1H$ NMR data were obtained by Special Data Services of Champaign, Il using a 400 MHz Varian spectrometer. Approximately 15 to 30 mg of each form was dissolved in $d_6$-DMSO, dried over molecular sieves, and placed in a 5 mm NMR tube, which had been dried at 250° C. for 6 hours. Data were collected at a $^1H$ resonant frequency of 399.798 MHz, with a 7 kHz sweep width/filter, 32K data points, and 40 acquisitions. Additional parameters included a 7 $\mu s$ $^1H$ pulse width and a 5 second pulse delay. The FID data was processed by zerofilling to 64K data points and multiplying by 0.2 Hz exponential line broadening prior to Fourier transformation. Predicted chemical shift values were based on teh structure using ChemDraw Pro.

F. Moisture Balance

Moisture sorption/desorption data were collected on a VTI SGA-100 moisture balance system. For sorption isotherms, a sorption range of 5 to 95% relative humidity (RH) and a desorption range of 95 to 5% RH in 10% RH increments was used for analysis. The samples were not dried prior to analysis. Equilibrium criteria used for analysis were less than 0.0100 weight % change in 5 minutes with a maximum equilibration time of 3 hours if the weight criterion was not met. Data were not corrected for the initial moisture content of the samples.

G. Karl Fischer Water Analysis

Karl Fischer (titrimetric) water analysis was performed by Galbraith Laboratories, Inc. of Knoxville, Tenn. according to U.S. Pharmacopoeia, vol. 24, method 921, U.S.P. Pharmacopeial Convention, Inc, Rockville, Md.). The polymorph was tested for water content by Karl Fischer titration using a coulometer according to the published procedure and the manufacturer's coulometer instructions.

It will be apparent to those skilled in the art that various modifications and variations can be made to the compounds, compositions, and methods of the present invention without departing from the spirit or scope of the invention. Thus, it is intended that the present invention cover the modifications and variations of this invention provided they come within the scope of the appended claims and their equivalents.

We claim:

1. A polymorphic form of 9-nitrocamptothecin, the polymorph being characterizable as having, by differential scanning calorimetry, an endotherm at between 175.5 and 177.5° C., an exotherm at between 181.7 and 183.7° C., and an IR spectrum with no absorption centered between 3625 $cm^{-1}$ and 3675 $cm^{-1}$.

2. A polymorphic form of 9-nitrocamptothecin according to claim 1, wherein the polymorphic form comprises more than a trace of water.

3. A polymorphic form of 9-nitrocamptothecin according to claim 1, further characterizable as having, by differential scanning calorimetry, an endotherm at between 176 and 177° C., and an exotherm at between 182.2 and 183.2° C.

4. A polymorphic form of 9-nitrocamptothecin according to claim 1, further characterizable as having, by differential scanning calorimetry, an endotherm at between 176.3 and 176.7° C., and an exotherm at between 182.5 and 182.9° C.

5. A polymorphic form of 9-nitrocamptothecin according to claim 1, further characterizable as having, by differential scanning calorimetry, an endotherm at between 176.4 and 176.6° C., and an exotherm at between 182.6 and 182.8° C.

6. A polymorphic form of 9-nitrocamptothecin according to claim 1, wherein the polylymorph is obtained by grinding.

7. A polymorphic form of 9-nitrocamptothecin, the polymorph being characterizable as having an X-ray powder diffraction pattern with diffraction lines at °2θ values 8.0 and 25.7 for Cu Kα radiation of wavelength 1.5406 Angstrom.

8. A polymorphic form of 9-nitrocamptothecin, the polymorph being crystallized from acetone or dichloromethane.

9. A polymorphic form of 9-nitrocamptothecin according to claim 8, the polymorph being characterizable as having, by differential scanning calorimetry, an endotherm at between 175.5 and 177.5° C., an exotherm at between 181.7 and 183.7° C., and an IR spectrum with no absorption centered between 3625 $cm^{-1}$ and 3675 $cm^{-1}$.

10. A polymorphic form of 9-nitrocamptothecin according to claim 8, the polymorph being characterizable as having an X-ray powder diffraction pattern with diffraction lines at °2θ values 8.0 and 25.7 for Cu Kα radiation of wavelength 1.5406 Angstrom.

11. A pharmaceutical composition comprising:

a pharmaceutical carrier; and a polymorphic form of 9-nitrocamptothecin, the polymorph being characterizable as having, by differential scanning calorimetry, an endotherm at between 175.5 and 177.5° C., an exotherm at between 181.7 and 183.7° C., and an IR spectrum with no absorption centered between 3625 $cm^{-1}$ and 3675 $cm^{-1}$.

12. A pharmaceutical composition according to claim 11, wherein the polymorphic form comprises more than a trace of water.

13. A pharmaceutical composition according to claim 11, further characterizable as having, by differential scanning calorimetry, an endotherm at between 176 and 177° C., and an exotherm at between 182.2 and 183.2° C.

14. A pharmaceutical composition according to claim 11, further characterizable as having, by differential scanning calorimetry, an endotherm at between 176.3 and 176.7° C., and an exotherm at between 182.5 and 182.9° C.

15. A pharmaceutical composition according to claim 11, further characterizable as having, by differential scanning calorimetry, an endotherm at between 176.4 and 176.6° C., and an exotherm at between 182.6 and 182.8° C.

16. A pharmaceutical composition according to claim 11, wherein the polymorph is obtained by grinding.

17. A pharmaceutical composition comprising:

a pharmaceutical carrier; and a polymorphic form of 9-nitrocamptothecin, the polymorph being characterizable as having an X-ray powder diffraction pattern with diffraction lines at °2θ values 8.0 and 25.7 for Cu Kα radiation of wavelength 1.5406 Angstrom.

18. A pharmaceutical composition comprising:

a pharmaceutical carrier; and a polymorphic form of 9-nitrocamptothecin, the polymorph being crystallized from acetone or dichloromethane.

19. A pharmaceutical composition according to claim 18, the polymorph being aracterizable as having, by differential scanning calorimetry, an endotherm at between 175.5 and 177.5° C., an exotherm at between 181.7 and 183.7° C., and an IR spectrum with no absorption centered between 3625 $cm^{-1}$ and 3675 $cm^{-1}$.

20. A pharmaceutical composition according to claim 18, the polymorph being characterizable as having an X-ray powder diffraction pattern with diffraction lines at °2η values 8.0 and 25.7 for Cu Kα radiation of wavelength 1.5406 Angstrom.

21. A method of preparing a polymorphic form of 9-nitrocamptothecin, the method comprising:

crystallizing 9-nitrocamptothecin from acetone or dichloromethane.

22. A method according to claim 21, wherein the resulting polymorph is characterizable as having, by differential scanning calorimetry, an endotherm at between 175.5 and 177.5° C., an exotherm at between 181.7 and 183.7° C., and an IR spectrum with no absorption centered between 3625 $cm^{-1}$ and 3675 $cm^{-1}$.

23. A method according to claim 21, wherein the resulting polymorph is characterizable as having an X-ray powder diffraction pattern with diffraction lines at °2θ values 8.0 and 25.7 for Cu Kα radiation of wavelength 1.5406 Angstrom.

* * * * *